US008222448B2

(12) United States Patent
Jodry et al.

(10) Patent No.: US 8,222,448 B2
(45) Date of Patent: *Jul. 17, 2012

(54) PROCESSES FOR PRODUCTION OF 2-BROMO-2,2-DIFLUOROETHANOL AND 2-(ALKYLCARBONYLOXY)-1,1-DIFLUOROETHANESULFONIC ACID SALT

(75) Inventors: Jonathan Joachim Jodry, Kawagoe (JP); Masashi Nagamori, Fujimino (JP); Yuji Hagiwara, Kawagoe (JP); Masaki Fujiwara, Kawagoe (JP); Satoru Narizuka, Saitama (JP)

(73) Assignee: Central Glass Company, Limited, Ube-shi (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/223,605

(22) Filed: Sep. 1, 2011

(65) Prior Publication Data
US 2011/0319652 A1 Dec. 29, 2011

Related U.S. Application Data

(63) Continuation of application No. 12/678,223, filed as application No. PCT/JP2008/066041 on Sep. 5, 2008, now Pat. No. 8,110,711.

(30) Foreign Application Priority Data

Sep. 18, 2007 (JP) ................... 2007-241606
Jul. 2, 2008 (JP) ................... 2008-172944

(51) Int. Cl.
C07C 69/54 (2006.01)
(52) U.S. Cl. ......... 560/150; 560/205; 560/222; 560/229
(58) Field of Classification Search .................. 560/205, 560/222, 229
See application file for complete search history.

(56) References Cited

U.S. PATENT DOCUMENTS

| 2,678,953 | A | 5/1954 | Conly |
| 2,852,554 | A | 9/1958 | England |
| 6,749,987 | B2 | 6/2004 | Kodama et al. |
| 6,893,792 | B2 | 5/2005 | Miya et al. |
| 7,435,526 | B2 | 10/2008 | Kodama et al. |
| 7,511,169 | B2 | 3/2009 | Ohsawa et al. |
| 2006/0228648 | A1 | 10/2006 | Ohsawa et al. |
| 2007/0003871 | A1 | 1/2007 | Kodama et al. |
| 2009/0069521 | A1 | 3/2009 | Nagai et al. |
| 2009/0148791 | A1 | 6/2009 | Kodama et al. |
| 2009/0234155 | A1 | 9/2009 | Oh et al. |
| 2009/0291390 | A1 | 11/2009 | Jung et al. |
| 2010/0035185 | A1 | 2/2010 | Hagiwara et al. |
| 2010/0304303 | A1 | 12/2010 | Maeda et al. |
| 2011/0034721 | A1 | 2/2011 | Hagiwara et al. |

FOREIGN PATENT DOCUMENTS

| EP | 1710230 | 10/2006 |
| JP | 2002-214774 A | 7/2002 |
| JP | 2004-4561 A | 1/2004 |
| JP | 2004-117959 A | 4/2004 |
| JP | 2007-145797 | 6/2007 |
| KR | 10-2006-0107340 A | 10/2006 |
| WO | WO 2006/121096 A1 | 11/2006 |
| WO | WO 2008/099869 A1 | 8/2008 |

OTHER PUBLICATIONS

Sunggak Kim et al., "Ate Complex from Dilsobutylaluminum Hydride and n-Butyllithium as a Powerful and Selective Reducing Agent for the Reduction of Selected Organic Compounds Containing Various Functional Groups", J. Org. Chem., 1984, pp. 1717-1724, vol. 49, 1984 American Chemical Society.
Korean Office Action dated Sep. 26, 2011 (Ten (10) pages).
J.M.G. Cowie, et al., "Novel single ion, comb-branched polymer electrolytes", Solid State Ionics, 1999, pp. 233-242, vol. 123.
International Search Report including partial translation and PCT/ISA/237 (Twelve (12) pages), Nov. 28, 2008.
Javier Gonzalez, et al.,Difluoromethylation of Alkenes via Borohydride Reduction of 1,3-Dibromo-1, 1-difluoroalkanes, Journal of Organic Chemistry, 1991, pp. 4322-4325, vol. 56.
Written Opinion of the International Searching Authority (seven (7) pages), Apr. 15, 2010.

Primary Examiner — Sikarl Witherspoon
(74) Attorney, Agent, or Firm — Crowell & Moring LLP

(57) ABSTRACT

Disclosed is a process for producing 2-bromo-2,2-difluoroethanol, which comprises reducing a bromodifluoroacetic acid derivative represented by the formula [1] by using an ate hydride complex as a reducing agent. 2-Bromo-2,2-difluoroethanol thus produced can be used as the starting material to carry out the esterification step, the sulfination step and the oxidation step in this order, thereby producing a 2-alkylcarbonyloxy-1,1-difluoroethanesulfonic acid salt, wherein A represents a substituted or unsubstituted linear, branched or cyclic alkoxy group having 1 to 20 carbon atoms, a substituted or unsubstituted aryloxy group having 6 to 15 carbon atoms, a heteroaryloxy group having 4 to 15 carbon atoms, or a halogen atom.

1 Claim, No Drawings

PROCESSES FOR PRODUCTION OF 2-BROMO-2,2-DIFLUOROETHANOL AND 2-(ALKYLCARBONYLOXY)-1, 1-DIFLUOROETHANESULFONIC ACID SALT

CROSS REFERENCE TO RELATED APPLICATIONS

This application is a continuation of co-pending U.S. application Ser. No. 12/678,223, filed Mar. 15, 2010, which is a national stage application of international patent application no. PCT/JP2008/066041, filed Sep. 5, 2008. Priority is claimed based on Japanese patent application no. 2007-241606, filed Sep. 18, 2007, and Japanese patent application no. 2008-172944, filed Jul. 2, 2008.

TECHNICAL FIELD

The present invention relates to a process for producing 2-bromo-2,2-difluoroethanol useful as an intermediate of medicines or agrichemicals, or as a synthetic intermediate or raw material for functional materials such as fluorine-containing polymers. Moreover, the present invention relates to a process for producing fluorine-containing sulfonates useful as: an intermediate for producing a photoacid generator useful as a chemically amplified resist material suitable for a micro-processing technology, particularly photolithography, in the production steps of semiconductor devices and the like; or an intermediate for producing solid electrolytes used in fuel cells or the like. Furthermore, the present invention relates to a process for producing fluorine-containing onium sulfonic acid salts that function as the photoacid generator.

BACKGROUND OF THE INVENTION

Hitherto, processes for producing 2-bromo-2,2-difluoroethanol, which have been known, had been very few. Patent Document 1 presents a description about producing 2-bromo-2,2-difluoroethanol by reacting a silver salt of 2,2-difluoro-3-hydroxypropionic acid with bromine.

[Chemical Formula 1]

EQUATION [1]

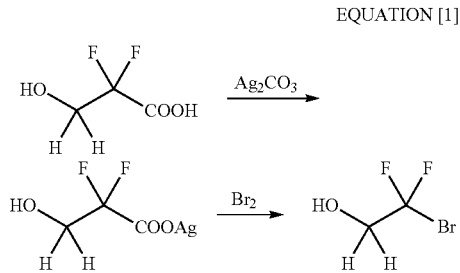

Additionally, solid polymer electrolytes used as electrolytes for fuel cells are being developed briskly in recent years. Most of these have a fluorine-containing sulfonic acid derivative at its end. Non-Patent Document 1 reports a solid polymer electrolyte formed by copolymerizing acrylate which has a fluorine-containing sulfonic acid lithium salt at its end.

Furthermore, in recent years, the trend toward micro-scale pattern rule has been increasing with the trend toward large-scale integration and high-speed of LSI. The trend toward a shorter wavelength of the exposure light source lies behind it. For example, it has become possible to mass-produce DRAM (dynamic random-access memory) of 64M-bit (processing dimension is 0.25 μm or less) by the wavelength shortening from mercury lamp i-line (365 nm) to KrF excimer laser (248 nm). Furthermore, in order to realize the production of DRAM's having integration degrees of 256M and 1G or greater, a lithography using ArF excimer laser (193 nm) has been used.

As a resist suitable for such exposure wavelength, "chemically amplified resist material" attracts much attention. This contains a radiosensitive acid generator (hereinafter referred to as "photoacid generator") which generates an acid by radiation irradiation (hereinafter, referred to as "exposure"), and is a pattern-forming material that forms a pattern by making a difference in solubility in developing agent between the exposed portion and the unexposed portion through a reaction using the acid generated by the exposure as a catalyst.

Also concerning a photoacid generator used for such a chemically amplified resist material, studies have been made variously. It has been known that, in a case where a photoacid generator as has been used for a conventional chemically amplified resist material whose light source is KrF excimer laser light to generate alkane or arenesulfonic acid is used as a component of the above-mentioned ArF-type chemically amplified resist material, the acid strength is not sufficient to cleave an acid-unstable group so as not to allow resolution entirely, or that the sensitivity is so low as to make it unsuitable for the device production.

Therefore, as the photoacid generator for the ArF-type chemically amplified resist material, those that generate perfluoroalkanesulfonic acid high in acid strength are commonly used; however, perfluorooctane sulfonate and derivatives thereof, which are known as PFOS abbreviated by their initials, causes problems of stability (non-degradability) stemmed from a C—F bond and of biological concentration and accumulation stemmed from hydrophobicity or lipophilicity. Additionally, perfluoroalkanesulfonic acid having 5 or more carbon atoms and derivatives thereof also begin to cause the above problems.

In order to address the above problems regarding PFOS, there has been developed, at all parts, partially fluorinated alkanesulfonic acids having a reduced degree of fluorine substitution. For instance, alkoxycarbonylfluoromethanesulfonic acid onium salts such as triphenylsulfonium methoxycarbonyldifluoromethane sulfonate (Patent Document 2), (4-methylphenyl)diphenylsulfonyl t-butoxycarbonyldifluoromethane sulfonate (Patent Document 3) and triphenylsulfonium (adamant-1-ylmethyl)oxycarbonyldifluoromethane sulfonate (Patent Document 4) have been developed as the acid generator.

On the other hand, triphenylsulfonium 1,1,3,3,3-pentafluoro-2-benzoyloxypropane-1-sulfonate, which is a kind of alkylcarbonyloxyalkanesulfonic acid onium salt and has an ester bond opposite to that of the above-mentioned alkoxycarbonyldifluoromethanesulfonic acid onium salt, and the like have been developed (Patent Document 5).

The present applicant has found 2-alkylcarbonyloxy-1,1-difluoroethanesulfonic acid onium salts represented by the formula [8] or [13], which has three less fluorine atoms than the acid generators presented by the Patent Documents so as to be considered to less affect the environment even though identical with alkylcarbonyloxyalkanesulfonic acid onium salt. Additionally, the present applicant found this substance to function as an acid generator having a high acid strength with the minimum possible number of fluorine atom, and to be excellent in compatibility with solvents or resins so as to be useful as the acid generator for the resist material, and already filed patent applications (Japanese Patent Application No. 2007-143879 and Japanese Patent Application No. 2007-143880).

By the way, as a process of synthesizing the above-mentioned alkoxycarbonyldifluoromethanesulfonic acid onium salt, a reaction path as represented by the following equation [2] has been known.

[Chemical Formula 2]

EQUATION [2]

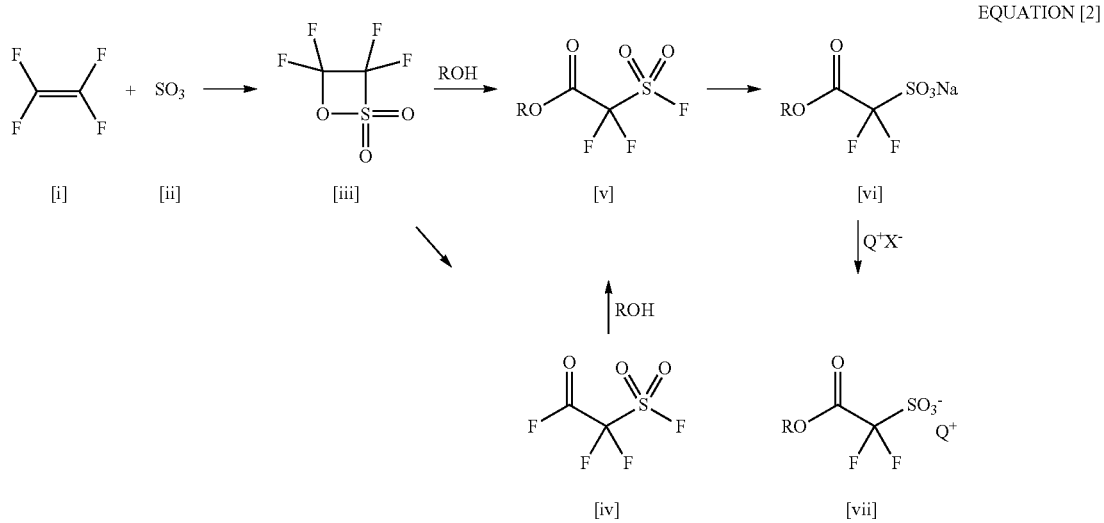

More specifically, the path including: synthesizing 3,3,4,4-tetrafluoro-[1,2]oxathietane 2,2-dioxide [iii] in the first place from tetrafluoroethylene [i] and sulfur trioxide [ii]; thereafter synthesizing [v] by a ring-opening reaction of [iii] with the use of alcohol (ROH), or passing 3,3,4,4-tetrafluoro-[1,2]oxathietane 2,2-dioxide [iv] through ring-opening isomerization of [iii] and then passing esterification of [iv] with the use of alcohol (ROH); subsequently converting [v] into a sulfonate (a sodium salt of sulfonic acid) [vi] with the use of a basic metal salt (mainly sodium hydroxide); and thereafter conducting an onium-salt exchange with the use of an onium salt ($Q^+X^-$: Q is a monovalent onium cation and X is mainly halogen) such as a sulfonium salt, thereby obtaining the target acid generator, alkoxycarbonyldifluoroalkanesulfonic acid onium salt [vii] (Patent Document 2 and Patent Document 6).

On the other hand, as a process of synthesizing an onium salt of 1,1,3,3,3-pentafluoro-2-benzoyloxypropane-1-sulfonic acid discussed in Patent Document 5, a reaction path as represented by the following equation [3] is disclosed.

[Chemical Formula 3]

EQUATION [3]

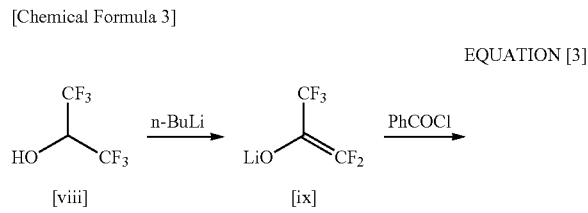

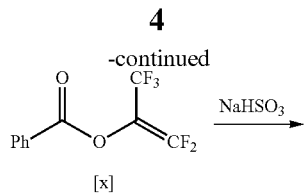

However, hitherto known processes for producing a 2-alkylcarbonyloxy-1,1-difluoroethanesulfonic acid salt have been very few, so that hitherto known processes for producing 2-(alkylcarbonyloxy)-1,1-difluoroethanesulfonic acid onium salt have been very few.

Patent Document 1: U.S. Pat. No. 2,678,953

Patent Document 2: Japanese Patent Application Publication No. 2004-117959

Patent Document 3: Japanese Patent Application Publication No. 2002-214774

Patent Document 4: Japanese Patent Application Publication No. 2004-4561

Patent Document 5: Japanese Patent Application Publication No. 2007-145797

Patent Document 6: U.S. Pat. No. 2,852,554

Non-Patent Document 1: Solid State Ionics, 1999, Volume 123, pages 233-242

SUMMARY OF THE INVENTION

A process disclosed in Non-Patent Document 1 with relation to the process for producing 2-bromo-2,2-difluoroethanol is not clear about details such as experimental conditions and yield, so as to be uncertain how useful the process is; however, the process uses an expensive silver salt as the starting material in any case, so that the industrialization thereof is expected to be difficult from the economical viewpoint. In addition to this, 2,2-difluoro-3-hydroxypropionic acid (the raw material for the silver salt) itself is not a compound of commercial-scale distribution to be enormously hard to get at the reagent level, so that the industrialization is considered to be hard.

The conventional production process of 2-bromo-2,2-difluoroethanol is thus extremely difficult, and therefore the establishment of the industrial production process efficient and performable for a long time to come has been desired.

Furthermore, the process for producing alkoxycarbonyldifluoromethanesulfonic acid salt, as shown in the equation [2] uses 3,3,4,4-tetrafluoro-[1,2]oxathietane 2,2-dioxide [iii] formed from tetrafluoroethylene [i] and sulfur trioxide [ii] as the raw material. Tetrafluoroethylene [i] is highly chemically reactive and has the danger of explosion, as commonly known, so as to be hard to handle in large quantity. Additionally, sulfur trioxide [ii] is an oxidizing agent so strong as to violently react with flammable substances, reducing substances and organic compounds, and therefore brings the load of handling in large quantity. As discussed above, in this process reagents having difficulty in handling in large quantity are mixed, so that an enough attention to safety is needed. This reaction is thus high in degree of industrial difficulty, which necessarily makes the obtained 3,3,4,4-tetrafluoro-[1,2]oxathietane 2,2-dioxide [iii] very expensive.

In addition, there is a problem of hydrogen fluoride or fluoride salt produced as a large quantity of by-product by the conversion reaction of the 3,3,4,4-tetrafluoro-[1,2]oxathietane 2,2-dioxide ([iv] or [v]). A fluorine ion liberated from hydrogen fluoride or fluoride salt corrodes and devitrifies a glass reactor. Additionally, not only hydrogen fluoride itself but also hydrogen fluoride (serving as a strong acid) generated by contact between fluoride salt and acid make metallic reactors such as iron and stainless steel unusable, so that usable materials for the reactors are greatly limited.

Thus, there exist some disadvantages in producing alkoxycarbonyldifluoromethanesulfonic acid salt.

On the other hand, in Patent Document 5, 1,1,1,3,3,3-hexafluoro-2-propanol [viii] having 6 fluorine atoms serves as the starting material to construct 1,1,3,3,3-pentafluoro-2-benzoyloxypropane-1-sulfonic acid salt [xi] as represented by the above equation [3]. Upon this, the sulfonic acid salt is led to be an onium salt of 1,1,3,3,3-pentafluoro-2-benzoyloxypropane-1-sulfonic acid [xii]. This synthesizing process is characterized by passing an enolate represented by [ix] as an intermediate active species. An enolate ion is, generally, a chemical species which is hard to exist stably. However, in the compound of Patent Document 5 whose $CF_3$ group bonding to carbon of C=C double bond has a strong electron-attracting property, the enolate is stabilized, with which the above reaction is allowed as a result.

Meanwhile, the substrate of the present invention whose moiety corresponding to this "$CF_3$ group" is "H" is therefore largely reduced in electron withdrawal against a double bond moiety. As a result, an enolate ion corresponding thereto becomes unstable so as to make it difficult to perform a reaction corresponding to the reaction of the Patent Document (as shown in the following equation).

[Chemical Formula 4]

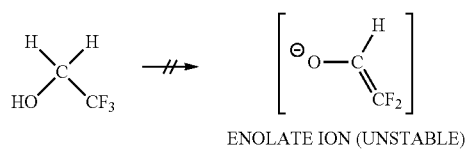

ENOLATE ION (UNSTABLE)

In actual fact, there has never been known a process for obtaining 2,2-difluoroethen-1-yl aliphatic acid carboxylate or aromatic carboxylate by using 2,2,2-trifluoroethanol as the starting material. Furthermore, there has never been found a report of forming an enolate salt [$CF_2$=CHOM (M=Li, K, Na)] serving as a precursor of these.

Concerning the production of alkylcarbonyloxyalkanesulfonic acid, a production process of 2-alkylcarbonyloxy-1,1-difluoroethanesufonic acid salt having 2 fluorine atoms has never been known, though a production process of compound having a high number of fluorine atoms such as 1,1,3,3,3-pentafluoro-2-benzoyloxypropane-1-sulfonic acid salt has been known.

In summary of the above, the difluoroalkanesulfonic acid skeleton having 2 fluorine atoms preferably serves as an alkanesulfonic acid salt having a sufficient acid strength with a lower number of fluorine atom; however, the conventional process of producing alkoxycarbonyldifluoromethanesulfonic acid salt has disadvantages, in which particularly the process of producing 2-alkylcarbonyloxy-1,1-difluoroethanesulfonic acid salt has never been known.

Consequently, the establishment of the industrial production process capable of economically and readily producing the difluoroalkanesulfonic acid skeleton having 2 fluorine atoms has been desired.

In view of the above, an object of the present invention is: to provide a process for economically and readily producing 2-bromo-2,2-difluoroethanol useful as an intermediate of medicines or agrichemicals from a commercially available raw material, in the first place; and to provide a process for producing 2-alkylcarbonyloxy-1,1-difluoroethanesulfonic acid salts useful as the photoacid generator used for the chemically amplified resist material, by using 2-bromo-2,2-difluoroethanol as the raw material.

The present inventors have eagerly made studies in order to achieve the above object. The present invention includes [Embodiment 1] to [Embodiment 4] as will be discussed below.

Embodiment 1

To begin with, studies were made on a process of synthesizing 2-bromo-2,2-difluoroethanol, a key compound common in all of the present invention.

In course thereof, it was invented before anything else to use an industrially economical and readily available bromodifluoroacetic acid derivative such as bromodifluoroacetic acid ester and bromodifluoroacetic acid halide as the starting material. It is, as represented by the following equation [4], a process for selectively reducing only a carbonyl group in the skeleton of bromodifluoroacetic acid ester or bromodifluoroacetic acid halide, without reducing a carbon-bromine bond of a bromodifluoromethyl group (while preventing debromination).

[Chemical Formula 5]

EQUATION [4]

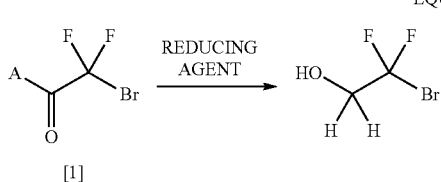

[1]

(In the above equation [4], A represents a substituted or unsubstituted linear, branched or cyclic alkoxy group having 1 to 20 carbon atoms, a substituted or unsubstituted aryloxy group having 6 to 15 carbon atoms or a heteroaryloxy group having 4 to 15 carbon atoms, or halogen(fluorine, chlorine, bromine, iodine).)

It is generally difficult to selectively reduce only a carbonyl group (while preventing debromination) in such a compound as to have both bromodifluoromethyl group and carbonyl group.

The present inventors actually carried out a hydrogenation reaction with the use of an activated carbon-carrying palladium catalyst, at the early stage of the studies. Upon this, the obtained as a result was not the target 2-bromo-2,2-difluoroethanol but principally ethyl difluoroacetate (see the following equation [5] and Comparative Example 1).

[Chemical Formula 6]

EQUATION [5]

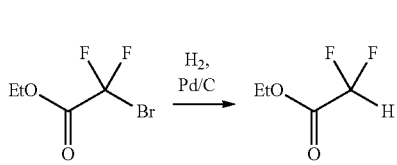

Then, against the same raw material, an active zinc was used as an reducing agent. In this case also, the obtained as a result was not the target 2-bromo-2,2-difluoroethanol but principally ethyl difluoroacetate (see the following equation [6] and Comparative Example 2).

[Chemical Formula 7]

EQUATION [6]

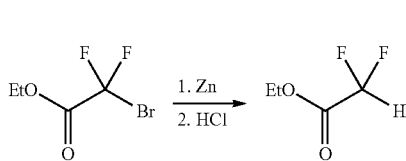

As a reducing agent capable of selectively reducing the carbonyl group, sodium borohydride (NaBH$_4$) which is a kind of ate hydride complexes is widely known. For example, a report is disclosed by Journal of Organic Chemistry, 1991, Volume 56, pages 4322-4325, in which 1,3-dibromo-1,1-difluoroalkanes are reduced in the use of sodium borohydride (NaBH$_4$) thereby obtaining 1,1-difluoroalkanes. An example of the reaction discussed in the document is represented by the following equation [7].

[Chemical Formula 8]

EQUATION [7]

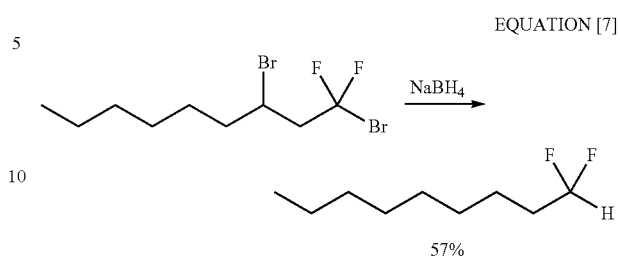

57%

It has been known that sodium borohydride (NaBH$_4$) thus acts on the bromodifluoromethyl group thereby causing debromination reaction in a reductive manner.

Furthermore, the present inventors reacted ethyl 6-bromo-5,5,6,6-tetrafluorohexanoic acid having both bromodifluoromethyl group and carbonyl group with sodium borohydride (NaBH$_4$). In this case also, a compound whose bromodifluoromethyl group was debrominated in a reductive manner (see the following equation [8] and Comparative Example 3).

[Chemical Formula 9]

EQUATION [8]

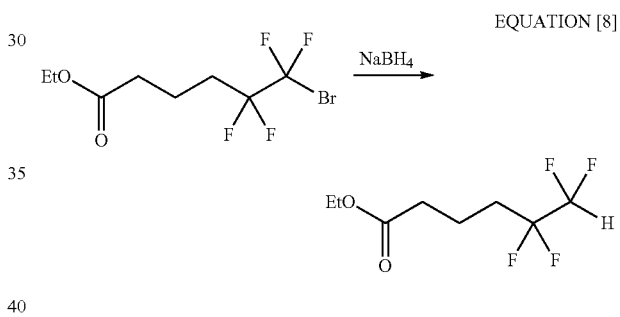

From the results of the above, it was expected to be difficult to use sodium borohydride (NaBH$_4$) for the selective reduction of carbonyl group of the bromodifluoroacetic acid derivative no matter how excellent sodium borohydride is as a carbonyl-selective reducing agent.

However, the present inventors found that the target 2-bromo-2,2-difluoroethanol could be specifically obtained at a selectivity of about 100% in spite of the above-mentioned expectation when conducting reduction on bromodifluoroacetic acid derivative represented by the formula [1] by using the ate hydride complex as the reducing agent For example, when conducting reduction on bromodifluoroacetic acid ester by using sodium borohydride (NaBH$_4$) (an ate hydride complex) as the reducing agent, 2-bromo-2,2-difluoroethanol can be obtained at a selectivity of about 100%. The further surprising fact is that it has become clear that 2-bromo-2,2-difluoroethanol is obtained at a selectivity of about 100% also in a case of using lithium aluminohydride (LiAlH$_4$) as well as the case of sodium borohydride (NaBH$_4$), the lithium aluminohydride being a kind of ate hydride complexes and said to have a reduction capability greater than that sodium borohydride has (see the following equation [9] and Examples 1 and 2).

[Chemical Formula 10]

EQUATION [9]

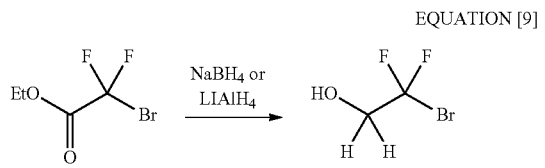

Moreover it has become clear, also concerning bromodifluoroacetic acid halide, that 2-bromo-2,2-difluoroethanol can be obtained by using sodium borohydride ($NaBH_4$) which is a kind of ate hydride complexes as the reducing agent (see Example 3).

The present inventors thus found a novel production process suitable for a large-scale production of 2-bromo-2,2-difluoroethanol useful as an organic intermediate.

Furthermore, the present inventors have eagerly made studies on synthesizing various kinds of 2-alkylcarbonyloxy-1,1-difluoroethanesulfonic acid salts by using 2-bromo-2,2-difluoroethanol produced by the above-mentioned process as the starting material ([Embodiment 2] to [Embodiment 4]).

Embodiment 2

The present inventors had reached a finding that 2-bromo-2,2-difluoroethanol obtained by the process of [Embodiment 1] (which is also referred to as "a 1st step") as represented by the equation [9] is first of all introduced in order into reactions of 2nd to 4th steps thereby producing a 2-alkylcarbonyloxy-1,1-dirluoroethanesulfonic acid salt represented by the equation [2] (Equation [10]).

[Chemical Formula 11]

EQUATION [10]

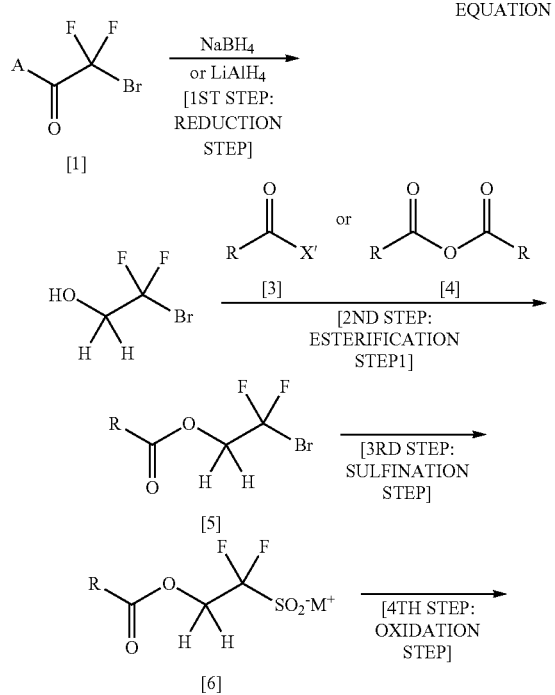

-continued

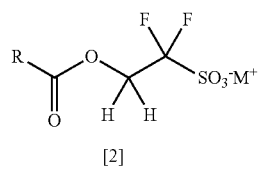

(In the above equation [10], A is synonymous with A represented in the equation [4]. R represents a substituted or unsubstituted linear, branched or cyclic alkyl group having 1 to 20 carbon atoms, a substituted or unsubstituted aryl group having 6 to 15 carbon atoms or a heteroaryl group having 4 to 15 carbon atoms. However, those having in its structure an unconjugated unsaturated moiety (a double or triple bond) as R, other than aromatic rings having a conjugated unsaturated moiety, such as aryl group and heteroaryl group, are excepted. X' represents a hydroxyl group or a halogen. $M^+$ represents a counter cation.)

More specifically, it has been found that; 2-bromo-2,2-difluoroethanol is produced in the above-mentioned reduction step (a 1st step); then, the compound is reacted with acids or acid halides represented in the formula [3] or acid anhydrides represented in the formula [4] thereby obtaining a carboxylic acid bromodifluoroethyl ester represented by the formula [5] (a 2nd step; an esterification step 1); then, the carboxylic acid bromodifluoroethyl ester is reacted in the presence of a sulfinating agent and a base so as to be converted into a 2-alkylcarbonyloxy-1,1-difluoroethanesulfinic acid salt represented by the formula [6] (a 3rd step: a sulfination step); and then the sulfinic acid salt is reacted with an oxidizing agent (a 4th step: an oxidation step) thereby obtaining a 2-alkylcarbonyloxy-1,1-difluoroethanesulfonic acid salt represented by the formula [2].

In order to obtain a 2-alkylcarbonyloxy-1,1-difluoroethanesulfonic acid salt represented by the formula [2], it is critically important to conduct the above-mentioned step in order. As shown in the following equation [11], there can be considered a process of carrying out a prior sulfination of 2-bromo-2,2-difluoroethanol, oxidation and then esterification and a process of carrying out a prior sulfination of 2-bromo-2,2-difluoroethanol, esterification and an oxidation in the end; however, the sulfination of 2-bromo-2,2-difluoroethanol is difficult to be done and therefore the adoption thereof is found not to be allowed (Comparative Example 4).

[Chemical Formula 12]

EQUATION [11]

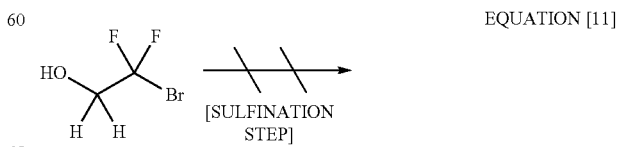

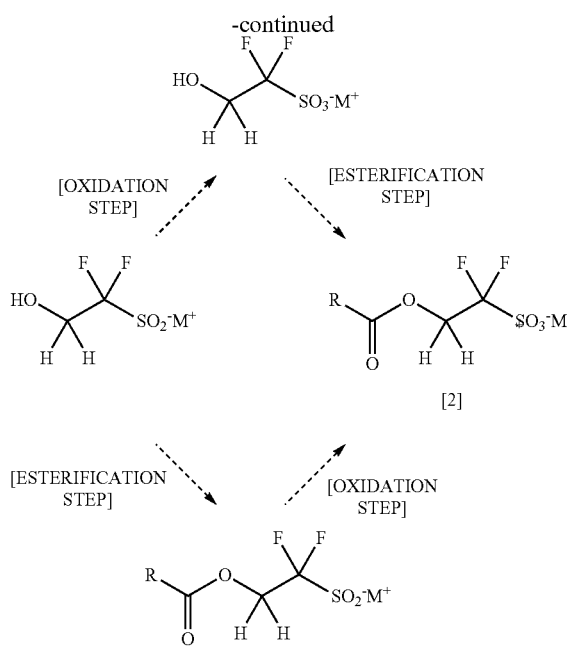

[2]

(In the above equation [11], R and M⁺ are synonymous with R and M⁺ represented in the equation [10].)

The present inventors thus found a novel production process suitable for a large-scale production of 2-alkylcarbonyloxy-1,1-difluoroethanesulfonic acid salt useful as an intermediate for producing a photoacid generator for a chemically amplified resist material or as an intermediate for producing a solid polymer electrolyte for fuel cells.

Embodiment 3

It has been found that the 2-alkylcarbonyloxy-1,1-dirluoroethanesulfonic acid salt represented by the equation [2] and synthesized by the process of [Embodiment 2] is introduced further into "an onium-salt exchanging step (a 5th step)" thereby obtaining a 2-alkylcarbonyloxy-1,1-difluoroethanesulfonic acid onium salt represented by the formula [8] (see the following equation [12]).

[Chemical Formula 13]

EQUATION [12]

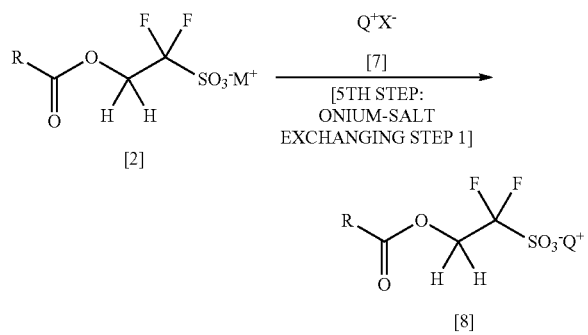

(In the above equation [12], R and M⁺ are synonymous with R and M⁺ represented in the equation [10]. X⁻ represents a monovalent anion. Q⁺ represents a sulfonium cation represented by the following formula (a) or the following formula (b) or an iodonium cation represented by the following formula (c).)

[Chemical Formula 14]

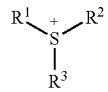

(a)

In the formula (a), $R^1$, $R^2$ and $R^3$ mutually independently represent a substituted or unsubstituted linear or branched alkyl group, alkenyl group or oxoalkyl group having 1 to 10 carbon atoms, or a substituted or unsubstituted aryl group, aralkyl group or aryloxoalkyl group having 6 to 18 carbon atoms. Furthermore, any two or more of $R^1$, $R^2$ and $R^3$ may bond to each other to form a ring together with a sulfur atom shown in the formula.

[Chemical Formula 15]

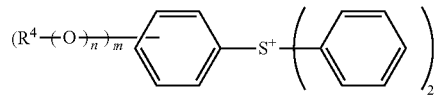

(b)

In the formula (b): $R^4$ represents a substituted or unsubstituted linear, branched or cyclic alkyl group or alkenyl group having 1 to 20 carbon atoms or a substituted or unsubstituted aryl group having 6 to 14 carbon atoms; m represents an integer of from 1 to 5; and n represents 0 (zero) or 1.

[Chemical Formula 16]

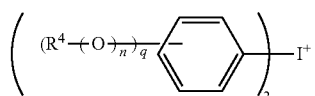

(c)

In the formula (c): $R^4$ represents a substituted or unsubstituted linear, branched or cyclic alkyl group or alkenyl group having 1 to 20 carbon atoms or a substituted or unsubstituted aryl group having 6 to 14 carbon atoms; q represents an integer of from 0 (zero) to 5; and n represents 0 (zero) or 1.

Namely, by the process of [Embodiment 3] the synthesis of 2-alkylcarbonyloxy-1,1-difluoroethanesulfonic acid onium salt useful as a photoacid generator used for a chemically amplified resist material has become possible.

Embodiment 4

As discussed above, R, a functional group of the compound synthesized in [Embodiment 3], is limited in kind. In other words, R, a functional group of the compound synthesized in [Embodiment 3], is "a substituted or unsubstituted linear, branched or cyclic alkyl group having 1 to 20 carbon atoms, a substituted or unsubstituted aryl group having 6 to 15 carbon atoms or a heteroaryl group having 4 to 15 carbon atoms", from which those having in its structure an unconjugated unsaturated moiety (a double or triple bond) as R, other than aromatic rings having a conjugated unsaturated moiety, such as aryl group and heteroaryl group, are excepted. This is derived from the 3rd step (the sulfination step). The present inventors has found it difficult to obtain the target sulfinated compound when using a compound having in its structure an unconjugated unsaturated moiety (a double or triple bond) as R as the raw material for the 3rd step (the sulfination step) because of a side reaction caused at the unconjugated unsaturated moiety.

Examples of R having an unconjugated unsaturated moiety (a double or triple bond) are linear, branched or cyclic alkenyl groups. Concrete examples of the alkenyl groups include vinyl group, allyl group, 1-methylethenyl group, 1-methylallyl group, 2-methylallyl group, 1-propenyl group, isopropenyl group, 2-butenyl group, 3-butenyl group, 1,3-butadienyl group, 2-pentenyl group, 4-pentenyl group, 2-hexenyl group, 5-hexenyl group, cyclopropenyl group, cyclopentenyl group, cyclohexenyl group and 5-norbornen-1-yl group (the following equation [13] and the equation [14]; Comparative Examples [5] and Comparative Examples [6]).

[Chemical Formula 17]

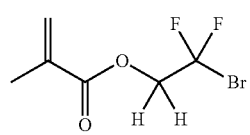

EQUATION [13]

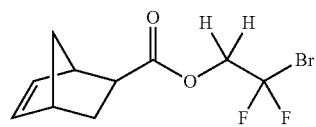

EQUATION [14]

In view of the above circumstances, the present inventors found a novel synthesis route in which a 2-alkylcarbonyloxy-1,1-difluoroethanesulfonic acid salt represented by the formula [2] and obtained in the above [Embodiment 2] is used as the starting material, and additionally reached the finding that the above problems are solved by taking this route.

More specifically, it has been found that a 2-alkylcarbonyloxy-1,1-difluoroethanesulfonic acid onium salt useful as a photoacid generator for a resist material and represented by the formula [13]

[Chemical formula 23]

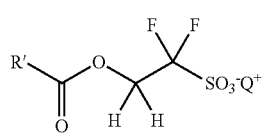

is obtained: by conducting saponification reaction (hydrolysis reaction in the presence of a basic substance) on the 2-alkylcarbonyloxy-1,1-difluoroethanesulfonic acid salt represented by the formula [2] and obtained by the above [Embodiment 2] (a 5'th step: a saponification step) thereby obtaining a 2-hydroxy-1,1-difluoroethanesulfonic acid salt represented by the formula [9]

[Chemical formula 18]

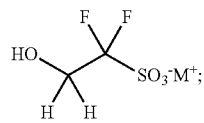

then by reacting it with a carboxylic acid derivative represented by the formula [10]

[Chemical formula 19]

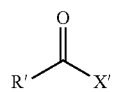

or the formula [11]

[Chemical formula 20]

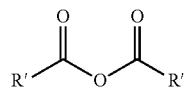

(a 6th step: an esterification step 2) thereby obtaining a 2-(alkylcarbonyloxy)-1,1-difluoroethanesulfonic acid salt represented by the formula [12]

[Chemical formula 21]

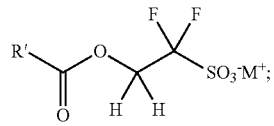

and then by conducting an onium-salt exchange thereon (a 7th step: an onium-salt exchanging step 2) by using a monovalent onium salt represented by the formula [7]

[Chemical formula 22]

$Q^+X^-$ [7]

(see the following equation [15]).

[Chemical Formula 24]

EQUATION [15]

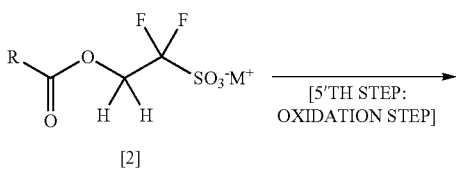

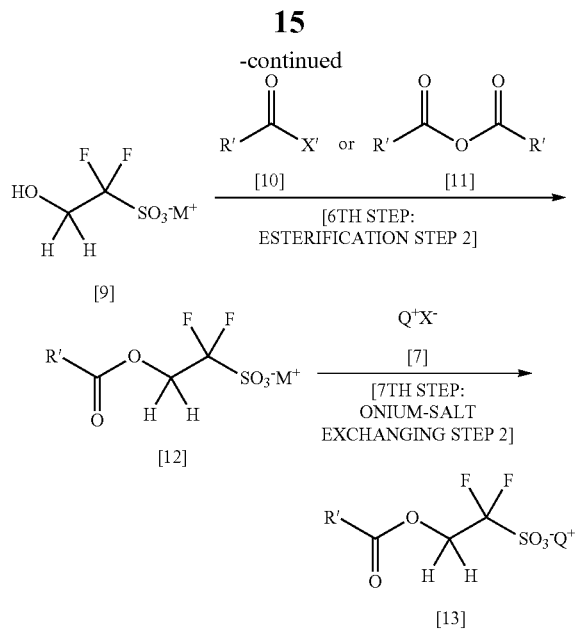

(In the above equation [15], M⁺ shown in the formula [9] and the formula [12] represents a counter cation. X' of the formula [10] is synonymous with X' of the formula [3]. In the formula [10] to the formula [13], R' represents a substituted or unsubstituted linear, branched or cyclic alkyl group having 1 to 20 carbon atoms, a substituted or unsubstituted linear, branched or cyclic alkenyl group having 1 to 20 carbon atoms, a substituted or unsubstituted aryl group having 6 to 15 carbon atoms or a heteroaryl group having 4 to 15 carbon atoms.)

In this finding, the important point is that R', a substituent for the 2-alkylcarbonyloxy-1,1-difluoroethanesulfonic acid onium salt represented by the formula [13], includes "those having in its structure an unconjugated unsaturated moiety (a double or triple bond)". Namely, this [Embodiment 5] is useful particularly for a 2-alkylcarbonyloxy-1,1-difluoroethanesulfonic acid onium salt having in its structure an unconjugated unsaturated moiety as a substituent R', among those useful as the photoacid generator for the chemically amplified resist material.

Particularly, those having an unconjugated unsaturated moiety at the end of the substituent, i.e. 2-(ω-alkenylcarbonyloxy)-1,1-difluoroethenesulfonic acid onium salts, can be fixed in a resist resin by being copolymerized with other monomer and therefore can be used as "a photoacid generator of a type carried by the resist resin", as well as a polymerizable and fluorine-containing sulfonic acid onium salt disclosed in International Patent Application Publication No. 2006/121096 A1. The "photoacid generator of the type carried by the resist resin" is a new type of photoacid generator who has recently been receiving attention because of its high performances such as a high resolution. In such a sense also, 2-(ω-alkenylcarbonyloxy)-1,1-difluoroethenesulfonic acid onium salts having an unconjugated unsaturated moiety at the end of its substituent are extremely useful.

As discussed above, [Embodiment 1] to [Embodiment 4] are suitably selected thereby allowing to produce compounds of wide kinds of substituents, such as: 2-bromo-2,2-difluoroethanol useful as an intermediate of medicines or agrichemicals; 2-alkylcarbonyloxy-1,1-difluoroethanesulfonic acid salts useful as an intermediate for a photoacid generator for a resist material or as an intermediate for an electrolyte for a fuel cell; and 2-alkylcarbonyloxy-1,1-difluoroethanesulfonic acid onium salts useful as a photoacid generator. The present invention has thus been completed.

Moreover, the present inventors have found novel compounds (triphenylsulfonium 1,1-difluoro-2-(2-methacryloyloxy)-ethanesulfonate and sodium 2-hydroxy-1,1-difluoroethanesulfonate) in the course of studying these reaction steps.

The present invention, in which all necessary raw materials are inexpensive and the operation in any of the steps is so convenience as to be able to perform with a less operational burden, is much more advantageous than the conventional means in terms of an industrial-scale production of the target 2-bromo-2,2-difluoroethanol or the target 2-alkylcarbonyloxy-1,1-difluoroethanesulfonic acid salts.

According to the present invention, there is provided a process for producing 2-bromo-2,2-difluoroethanol (a first process) which process comprises a step of reducing a bromodifluoroacetic acid derivative represented by the formula [1] by using an ate hydride complex as a reducing agent.

[Chemical formula 25]

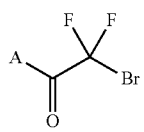

[1]

(In the above formula [1], A represents a substituted or unsubstituted linear, branched or cyclic alkoxy group having 1 to 20 carbon atoms, a substituted or unsubstituted aryloxy group having 6 to 15 carbon atoms or heteroaryloxy group having 4 to 15 carbon atoms, or halogen.)

Furthermore, according to the present invention, there is provided a process for producing a 2-(alkylcarbonyloxy)-1,1-difluoroethanesulfonic acid salt represented by the formula [2] (a second process)

[Chemical formula 26]

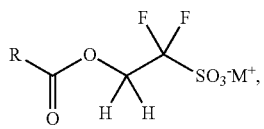

[2]

which process comprises the following four steps: a 1st step (a reduction step) of reducing a bromodifluoroacetic acid derivative represented by the formula [1]

[Chemical formula 27]

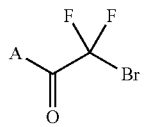

[1]

by using an ate hydride complex as a reducing agent, thereby producing 2-bromo-2,2-difluoroethanol; a 2nd step (an esterification step 1) of reacting the 2-bromo-2,2-difluoroethanol obtained by the 1st step (the reduction step) with a carboxylic acid derivative represented by the formula [3]

[Chemical formula 28]

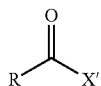

or the formula [4]

[Chemical formula 29]

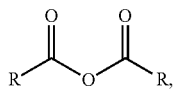

thereby obtaining a carboxylic acid bromodifluoroethyl ester represented by the formula [5]

[Chemical formula 30]

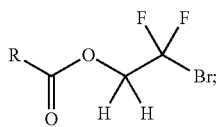

a 3rd step (a sulfination step) of reacting the carboxylic acid bromodifluoroethyl ester represented by the formula [5] and obtained by the 2nd step (the esterification step 1) with a base in the presence of a sulfinating agent, thereby obtaining a 2-(alkylcarbonyloxy)-1,1-difluoroethanesulfinic acid salt represented by the formula [6]

[Chemical formula 31]

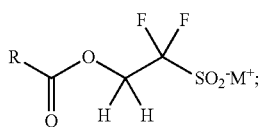

a 4th step (an oxidation step) of reacting the 2-(alkylcarbonyloxy)-1,1-difluoroethanesulfinic acid salt represented by the formula [6] and obtained by the 3rd step (the sulfination step) with an oxidizing agent thereby obtaining a 2-(alkylcarbonyloxy)-1,1-difluoroethanesulfonic acid salt represented by the formula [2].

(In the above formula [1], A represents a substituted or unsubstituted linear, branched or cyclic alkoxy group having 1 to 20 carbon atoms, a substituted or unsubstituted aryloxy group having 6 to 15 carbon atoms or heteroaryloxy group having 4 to 15 carbon atoms, or halogen. In the formula [2] to the formula [6], R represent a substituted or unsubstituted linear, branched or cyclic alkyl group having 1 to 20 carbon atoms, a substituted or unsubstituted aryl group having 6 to 15 carbon atoms or heteroaryl group having 4 to 15 carbon atoms; however, those having in its structure an unconjugated unsaturated moiety (a double or triple bond) as R are excepted. In the formula [3], X' represents hydroxyl group or halogen. In the formula [2] or the formula [6], M$^+$ represents a counter cation.)

Furthermore, according to the present invention, there is provided a process for producing a 2-(alkylcarbonyloxy)-1,1-difluoroethanesulfonic acid onium salt represented by the formula [8] (a third process)

[Chemical formula 33]

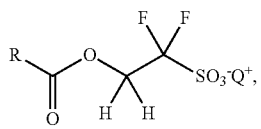

comprising: a step of conducting an onium-salt exchange (a 5th step: an onium-salt exchanging step 1) on the 2-(alkylcarbonyloxy)-1,1-difluoroethanesulfonic acid salt represented by the formula [2] and obtained by the process as claimed in Claim 2, by using a monovalent onium salt represented by the formula [7].

[Chemical formula 32]

$$Q^+X^- \quad [7]$$

(In the formula [7], X$^-$ represents a monovalent anion. In the formula [8], R is synonymous with R of the formula [2] to the formula [6]. In the formula [7] and the formula [8], Q$^+$ represents a sulfonium cation represented by the following formula (a) or the following formula (b), or an iodonium cation represented by the following formula (c).

[Chemical formula 34]

In the formula (a), R$^1$, R$^2$ and R$^3$ mutually independently represent a substituted or unsubstituted linear or branched alkyl group, alkenyl group or oxoalkyl group having 1 to 10 carbon atoms, or a substituted or unsubstituted aryl group, aralkyl group or aryloxoalkyl group having 6 to 18 carbon atoms. Furthermore, any two or more of R$^1$, R$^2$ and R$^3$ may bond to each other to form a ring together with a sulfur atom shown in this formula.

[Chemical formula 35]

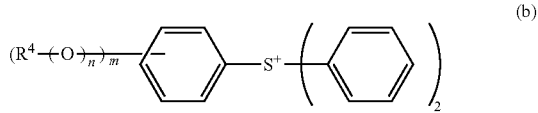

In the formula (b), R$^4$ represents a substituted or unsubstituted linear, branched or cyclic alkyl group or alkenyl group having 1 to 20 carbon atoms or a substituted or unsubstituted aryl group having 6 to 14 carbon atoms. m represents an integer of from 1 to 5, and n represents 0 (zero) or 1.

[Chemical formula 36]

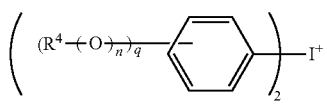
(c)

In the formula (c), $R^4$ represents a substituted or unsubstituted linear, branched or cyclic alkyl group or alkenyl group having 1 to 20 carbon atoms or a substituted or unsubstituted aryl group having 6 to 14 carbon atoms. q represents an integer of from 0 (zero) to 5, and n represents 0 (zero) or 1.

Furthermore, according to the present invention, there is provided a process for producing a 2-(alkylcarbonyloxy)-1,1-difluoroethanesulfonic acid onium salt represented by the formula [13] (a fourth step)

[Chemical formula 42]

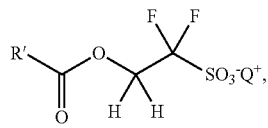
[13]

comprising: a step (a 5'th step: a saponification step) of saponifying the 2-(alkylcarbonyloxy)-1,1-difluoroethanesulfonic acid salt represented by the formula [2] and obtained by the process as claimed in Claim 2 thereby obtaining a 2-hydroxy-1,1-difluoroethanesulfonic acid salt represented by the formula [9]

[Chemical formula 37]

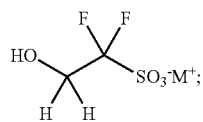
[9]

a step (a 6th step: an esterification step 2) of reacting the 2-hydroxy-1,1-difluoroethanesulfonic acid salt with a carboxylic acid derivative represented by the formula [10]

[Chemical formula 38]

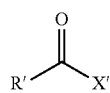
[10]

or the formula [11]

[Chemical formula 39]

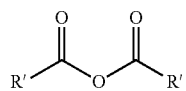
[11]

thereby obtaining a 2-(alkylcarbonyloxy)-1,1-difluoroethanesulfonic acid salt represented by the formula [12]

[Chemical formula 40]

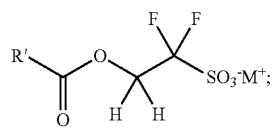
[12]

and a step of conducting an onium-salt exchange on the 2-(alkylcarbonyloxy)-1,1-difluoroethanesulfonic acid salt by using a monovalent onium salt represented by the formula [7].

[Chemical formula 41]

$Q^+X^-$     [7].

(In the formula [9] and the formula [12], $M^+$ represents a counter cation. In the formula [10], X' is synonymous with X' of the formula [3]. In the formula [10] to the formula [13], R' represents a substituted or unsubstituted linear, branched or cyclic alkyl group having 1 to 20 carbon atoms, a substituted or unsubstituted linear, branched or cyclic alkenyl group having 1 to 20 carbon atoms, a substituted or unsubstituted aryl group having 6 to 15 carbon atoms or heteroaryl group having 4 to 15 carbon atoms. In the formula [13], Q is synonymous with Q of the formula [7] and the formula [8].)

In the reduction step of the first or second process, the ate hydride complex used as the reducing agent may be a hydride complex based on boron hydride or aluminum hydride.

Furthermore in the reduction step of the first or second process, the ate hydride complex used as the reducing agent is sodium borohydride or lithium aluminohydride.

Furthermore, in the reduction step of the first or second process, the bromodifluoroacetic acid derivative may be a bromodifluoroacetic acid derivative represented by the formula [14].

[Chemical formula 43]

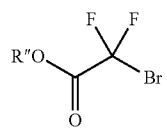
[14]

(In the formula [14], R" represents a substituted or unsubstituted linear, branched or cyclic alkyl group having 1 to 6 carbon atoms.)

Furthermore, according to the present invention, there is provided triphenylsulfonium 1,1-difluoro-2-(2-methacryloyloxy)-ethanesulfonate which is a novel compound corresponding to the 2-(alkylcarbonyloxy)-1,1-difluoroethanesulfonic acid onium salt represented by the formula [13].

Furthermore, according to the present invention, there is provided sodium 2-hydroxy-1,1-difluoroethanesulfonate which is a novel compound corresponding to the 2-hydroxy-1,1-difluoroethanesulfonic acid salt represented by the formula [9].

DETAILED DESCRIPTION

According to the present invention, 2-bromo-2,2-difluoroethanol (useful as an intermediate of medicines or agrichemicals or as a synthetic intermediate or raw material for functional materials such as fluorine-containing polymers and the like) can be produced from a bromodifluoroacetic acid derivative available at low cost, in only one convenient process step at a high yield and on an industrial scale, which is an effect of the present invention. Additionally, fluorine-containing sulfonic acid salts (useful as an intermediate for producing a solid electrolyte used for a fuel cell or the like or an intermediate for producing a photoacid generator useful as a chemically amplified resist material suitable for micromachining techniques (e.g. photolithography in particular) applied in industrial processes of a semiconductor device or the like) can be produced conveniently at a high yield and at an industrial scale by using 2-bromo-2,2-difluoroethanol as a raw material, which is a further effect of the present invention. Moreover, fluorine-containing sulfonic acid onium salts that function as the photoacid generator can be produced conveniently at a high yield and at an industrial scale, which is a still further effect of the present invention.

Hereinafter, the present invention will be discussed in more detail. The present invention includes, as represented by the following equation [16], five steps comprising: a step of reducing a bromodifluoroacetic acid derivative represented by the formula [1] by using an ate hydride complex as a reducing agent, thereby producing 2-bromo-2,2-difluoroethanol (an objective of the embodiment 1 of the present invention) (a 1st step; a reduction step); a step of esterifying the thus obtained 2-bromo-2,2-difluoroethanol thereby obtaining a carboxylic acid bromodifluoroethyl ester represented by the formula [5] (a 2nd step: an esterification step); a step of reacting the thus obtained carboxylic acid bromodifluoroethyl ester represented by the formula [5] in the presence of a sulfinating agent thereby obtaining a 2-alkylcarbonyloxy-1,1-difluoroethanesulfinic acid salt represented by the formula [6] (a 3rd step: a sulfination step); a step of reacting the thus obtained 2-alkylcarbonyloxy-1,1-difluoroethanesulfinic acid salt represented by the formula [6] with an oxidizing agent thereby obtaining a 2-alkylcarbonyloxy-1,1-difluoroethanesulfonic acid salt (an objective of the embodiment 2 of the present invention) represented by the formula [2] (a 4th step: an oxidation step); and a step of

[Chemical Formula 44]

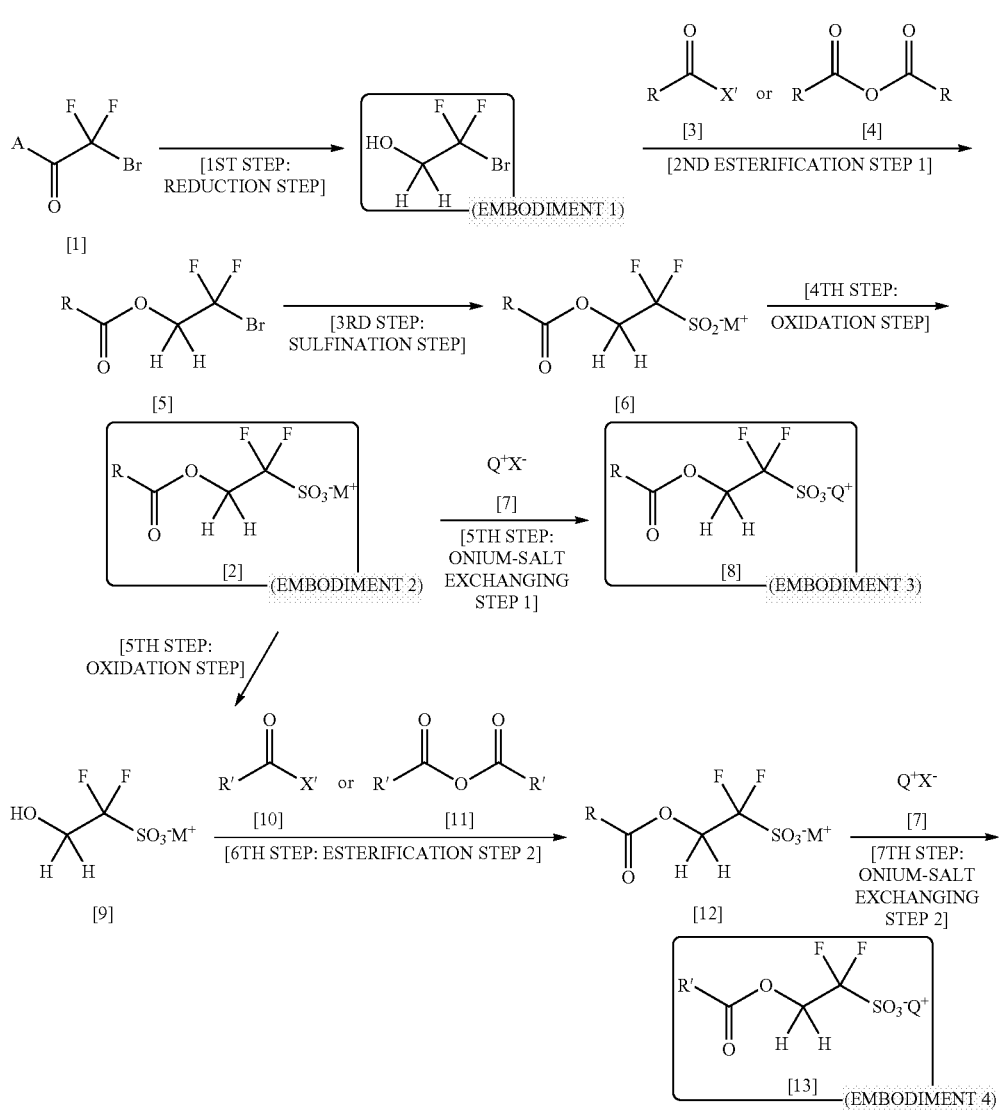

carrying out an onium-salt exchange on the thus obtained 2-alkylcarbonyloxy-1,1-difluoroethanesulfonic acid salt represented by the formula [2] by using a monovalent onium salt represented by the formula [7], thereby obtaining a 2-alkylcarbonyloxy-1,1-difluoroethanesulfonic acid onium salt (an objective of the embodiment 3 of the present invention) represented by the formula [8] (a 5th step: an onium-salt exchanging step 1). Upon undergoing these steps, a 2-alkylcarbonyloxy-1,1-difluoroethanesulfonic acid onium salt not having an unconjugated unsaturated moiety (a double or triple bond) as R of the formula [8] can be obtained.

Those having the unconjugated unsaturated moiety (the double or triple bond) can be obtained by undergoing three steps comprising: a step of saponifying the 2-alkylcarbonyloxy-1,1-difluoroethanesulfonic acid salt represented by the formula [2] thereby obtaining a 2-hydroxy-1,1-difluoroethanesulfonic acid salt represented by the formula [9] (a 5'th step: a saponification step); a step of esterifying the thus obtained 2-hydroxy-1,1-difluoroethanesulfonic acid salt represented by the formula [9] thereby producing a 2-alkylcarbonyloxy-1,1-difluoroethanesulfonic acid salt represented by the formula [12] (a 6th step: an esterification step 2); and a step of carrying out a further onium-salt exchange by using a monovalent onium salt represented by the formula [7] (a 7th step: an onium-salt exchanging step 2). In such a manner that a bromodifluoroacetic acid derivative represented by the formula [1] undergoes the seven steps, a 2-alkylcarbonyloxy-1,1-difluoroethanesulfonic acid onium salt having an unconjugated unsaturated moiety (a double or triple bond) as R of the formula [13] also can be obtained.

Hereinafter, each of the steps will be discussed in detail. To begin with, the 1st step of the present invention will be discussed. The 1st step is a step of reducing a bromodifluoroacetic acid derivative represented by the formula [1] by using an ate hydride complex as a reducing agent thereby producing 2-bromo-2,2-difluoroethanol (a reduction step).

Bromodifluoroacetic acid derivative represented by the formula [1], which is the starting material of the present invention, is bromodifluoroacetic acid ester or bromodifluoroacetic acid halide. Concrete examples of bromodifluoroacetic acid ester are methyl bromodifluoroacetate, ethyl bromodifluoroacetate, n-propyl bromodifluoroacetate, i-propyl bromodifluoroacetate, n-butyl bromodifluoroacetate, s-butyl bromodifluoroacetate, i-butyl bromodifluoroacetate, t-butyl bromodifluoroacetate, n-pentyl bromodifluoroacetate, n-hexyl bromodifluoroacetate, cyclohexyl bromodifluoroacetate, phenyl bromodifluoroacetate, and benzyl bromodifluoroacetate. Examples of bromodifluoroacetic acid halide include fluoride bromodifluoroacetate, chloride bromodifluoroacetate, bromide bromodifluoroacetate and iodide bromodifluoroacetate. Among these, the preferable in view of availability are methyl bromodifluoroacetate, ethyl bromodifluoroacetate, n-propyl bromodifluoroacetate, i-propyl bromodifluoroacetate, fluoride bromodifluoroacetate, chloride bromodifluoroacetate and bromide bromodifluoroacetate. The more preferable are ethyl bromodifluoroacetate, fluoride bromodifluoroacetate and chloride bromodifluoroacetate. If taking handiness (volatility and a bad smell of acid halide) into account, the most preferable is ethyl bromodifluoroacetate.

The ate hydride complex used as a reducing agent in the 1st step includes boron hydrides such as sodium borohydride (NaBH$_4$), lithium borohydride (LiBH$_4$), sodium cyanoborohydride (NaBH$_3$CN), zinc borohydride (Zn(BH$_4$)$_2$), potassium tri-sec-butylborohydride (K-selectride), and lithium tri-sec-butylborohydride (L-selectride), which have been commonly used. Also included are aluminum hydrides such as lithium aluminohydride (LiAlH$_4$), lithium tri-sec-butoxyaluminohydride (LiAlH(Ot-C$_4$H$_9$)$_3$), lithium trimethoxyaluminohydride (LiAlH(OCH$_3$)$_3$), diisobutylaluminum hydride ((i-C$_4$H$_9$)$_2$AlH) and sodium bis(methoxyethoxy)aluminumhydride (NaAlH$_2$(OCH$_2$CH$_2$OCH$_3$)$_2$), which have been commonly used. Among these, the preferable in views of economy, handiness and availability are sodium borohydride (NaBH$_4$), lithium aluminohydride (LiAlH$_4$), lithium tri-sec-butoxyaluminohydride (LiAlH(Ot-C$_4$H$_9$)$_3$), diisobutylaluminum hydride ((i-C$_4$H$_9$)$_2$AlH) and sodium bis(methoxyethoxy)aluminumhydride (NaAlH$_2$(OCH$_2$CH$_2$OCH$_3$)$_2$). The particularly preferable are sodium borohydride (NaBH$_4$) and lithium aluminohydride (LiAlH$_4$).

An amount of the reducing agent to be used, relative to 1 mole of bromodifluoroacetic acid derivative, is preferably not less than the number of moles determined by the following [Equation 1].

The required number of moles of the reducing agent=2/the number of active hydrogen atoms included in a molecule of the reducing agent     [Equation 1]

More specifically, the required number of moles is not less than 0.5 mole in the cases of sodium borohydride (NaBH$_4$) and of lithium aluminohydride (LiAlH$_4$); not less than 2.0 moles in the cases of lithium tri-sec-butoxyaluminohydride (LiAlH(Ot-C$_4$H$_9$)$_3$) and of diisobutylaluminum hydride ((i-C$_4$H$_9$)$_2$AlH); and not less than 1.0 mole in the case of sodium bis(methoxyethoxy)aluminumhydride (NaAlH$_2$(OCH$_2$CH$_2$OCH$_3$)$_2$). A used amount of these reducing agents is preferably 1 to 3 times the required number of moles, though normally 0.8 to 5 times the required number of moles. A used amount of exceeding the above range is surely allowed, but not preferable since it may cause a side reaction (such as reduction of a carbon-bromine bond of bromodifluoromethyl group), depending on the conditions.

These reducing agents may be used singly or in combination of not less than two kinds of these in a coexistent manner. However, coexistence of other than the above-mentioned ate hydride complexes is not preferable. Particularly, reducing agents that have hitherto been reported to reduce the bromine-carbon bond thereby causing debromination are not preferable. Concrete examples thereof are active zinc and metallic sodium. Additionally, sodium hydride (NaH) and lithium hydride (LiH), both of which are hydride type reducing agents but do not apply to the "ate" hydride complex, are also not preferable since these are excessively strong as a reducing agent. It is particularly preferable not to allow the coexistence of the reducing agents which do not apply to the "ate hydride complex" in the system at all. In the event that these coexist in the form of impurities, the amount thereof is preferably less than 0.1 mole and particularly preferably less than 0.05 mole relative to 1 mole of the above-mentioned "ate hydride complex".

In this step, a normal solvent is used. Examples of the solvent include: water; DMF; N,N-dimethyl sulfoxide (DMSO); alcohols such as methanol, ethanol and 2-propanol; ethers such as diethyl ether, tetrahydrofuran, dioxane, butyl methyl ether and diisopropyl ether; alkanes such as n-pentane, n-hexane, n-heptane and n-octane; and aromatic compounds such as benzene, toluene and xylene; however, the examples are not limited to these. Moreover, these solvents may be used singly or in combination of not less than two kinds thereof.

The preferably used solvent differs according to the used reducing agent and reaction substrate. For example, in the case of using sodium borohydride (NaBH$_4$), water may be used if the reaction substrate is water-soluble. If the reaction substrate is not water-soluble, however, alcohols such as methanol, ethanol and 2-propanol and ethers such as diethyl ether, tetrahydrofuran, dioxane, butyl methyl ether and diisopropyl ether are preferable, and additionally methanol, tetrahydrofuran and diisopropyl ether are particularly preferable. In the case of using lithium aluminohydride (LiAlH$_4$) alcohols are not preferable while ethers such as diethyl ether, tetrahydrofuran, dioxane, butyl methyl ether and diisopropyl ether are preferable. Among these, tetrahydrofuran and diisopropyl ether are particularly preferable.

The reaction can be conducted in air, but preferably conducted in an inert gas such as nitrogen and argon. In this step, the reaction temperature ranges normally from −100 to 200° C., preferably from −78 to 100° C., and more preferably from 0 to 70° C. Furthermore, the reaction time ranges about from 5 minutes to 24 hours; however, it is preferable that a temporal point at which the raw material bromodifluoroacetic acid derivative is consumed is determined, by analytical devices such as gas chromatography (GC) and nuclear magnetic resonance (NMR), as the endpoint of the reaction.

Upon termination of the reaction, 2-bromo-2,2-difluoroethanol can be obtained by normal means including extraction, distillation and the like. Moreover, it can be purified by column chromatography, precise distillation or the like, as necessary.

Then the 2nd step of the present invention will be discussed. The 2nd step is a step of reacting the obtained 2-bromo-2,2-difluoroethanol with a carboxylic acid derivative represented by the formula [3] or the formula [4] to cause esterification thereby obtaining a carboxylic acid bromodifluoroethyl ester represented by the formula [5] (the esterification step 1).

In the formula [3] or the formula [4], R represents a substituted or unsubstituted linear, branched or cyclic alkyl group having 1 to 20 carbon atoms, a substituted or unsubstituted aryl group having 6 to 15 carbon atoms or heteroaryl group having 4 to 15 carbon atoms. However, those having in its structure an unconjugated unsaturated moiety (a double or triple bond) as R are excepted. Additionally, X' as shown in the formula [3] represents hydroxyl group or halogen (fluorine, chlorine, bromine or iodine).

Concrete examples of R as shown in the formula [3] or the formula [4] are methyl group, ethyl group, n-propyl group, isopropyl group, cyclopropyl group, n-butyl group, sec-butyl group, isobutyl group, tert-butyl group, n-pentyl group, cyclopentyl group, n-hexyl group, 2-ethylhexyl group, cyclohexyl group, n-octyl group, n-decyl group, n-dodecyl group, 1-adamantyl group, 2-adamantyl group, bicyclo[2.2.1]hepten-2-yl group, 1-adamantanemethyl group, 2-adamantanemethyl group, phenyl group, 4-methoxyphenyl group, 4-tert-butylphenyl group, 4-biphenyl group, 1-naphthyl group, 2-naphthyl group, 10-anthranyl group and 2-furanyl group. Examples of R including carbonyl group, lactone and hydroxyl group are as follows:

[Chemical Formula 45]

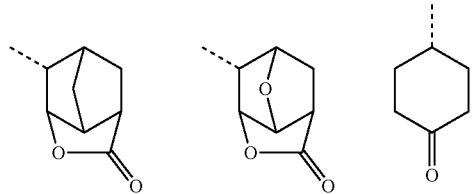

-continued

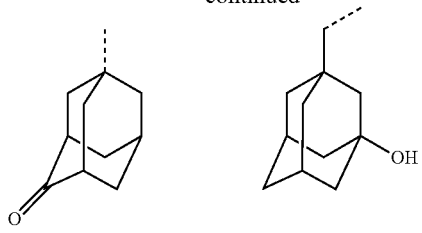

(Each dotted line represents a bonding moiety.)

A concrete process for producing carboxylic acid bromodifluoroethyl ester represented by the formula [5] by reacting 2-bromo-2,2-difluoroethanol obtained in the 1st step with carboxylic acids and carboxylic acid halides represented by the formula [3] or carboxylic acid anhydrides represented by the formula [4] is not particularly limited and therefore adopted from any of commonly known esterification processes.

Examples of the esterification processes are: a process of dehydrating condensation of a carboxylic acid represented by the formula [3] (X'=OH) and 2-bromo-2,2-difluoroethanol in the presence of an acid catalyst (Fischer esterification); and a process of reacting 2-bromo-2,2-difluoroethanol obtained in the 1st step with carboxylic acid halides (X'=Cl, Br, I, F) represented by the formula [3] or carboxylic acid anhydrides represented by the formula [4].

When using a carboxylic acid represented by the formula [3] (X'=OH), the carboxylic acid which is to act on 2-bromo-2,2-difluoroethanol and represented by the formula [3] is used normally in an amount ranging from 0.1 to 5 moles, preferably from 0.2 to 3 moles and more preferably from 0.5 to 2 moles relative to 1 mole of 2-bromo-2,2-difluoroethanol. It is particularly preferable to use the carboxylic acid in an amount within a range of from 0.8 to 1.5 moles.

Normally in the reaction, an aprotic solvent such as dichloroethane, toluene, ethylbenzene, monochlorobenzene, acetonitrile and N,N-dimethylformamide is used. These solvents may be used singly or in combination of not less than two kinds thereof.

The reaction temperature is normally within a range of from 0 to 200° C., preferably from 20 to 180° C., and more preferably from 50 to 150° C. It is preferable to conduct the reaction while stirring.

The reaction time depends on the reaction temperature; however, it ranges normally from several minutes to 100 hours, preferably from 30 minutes to 50 hours and more preferably from 1 to 20 hours. It is preferable that a temporal point at which the raw material 2-bromo-2,2-difluoroethanol is consumed is determined, by analytical devices such as gas chromatography (GC) and nuclear magnetic resonance (NMR), as the endpoint of the reaction.

Normally, this reaction is conducted with the addition of an organic acid such as para-toluenesulfonic acid and/or an inorganic acid such as sulfuric acid, as an acid catalyst. Moreover, 1,1'-carbonyldiimidazole, N,N'-dicyclohexylcarbodiimide or the like may be added as a dehydrating agent. An amount of the acid catalyst to be used is not particularly limited but preferably within a range of from 0.0001 to 10 moles, preferably from 0.001 to 5 moles and more preferably from 0.01 to 1.5 mole relative to 1 mole of 2-bromo-2,2-difluoroethanol.

When esterification reaction using the acid catalyst is conducted while carrying out dehydration, for example, by using Dean-Stark apparatus, the reaction time tends to be shortened, which is preferable.

Upon termination of the reaction, carboxylic acid bromodifluoroethyl ester represented by the formula [5] can be obtained by normal means including extraction, distillation, recrystallization and the like. Moreover, it can be purified by column chromatography, recrystallization or the like, as necessary.

On the other hand, in the case of using carboxylic acid halides represented by the formula [3] or carboxylic acid anhydrides represented by the formula [4], a used amount of the carboxylic acid halides represented by the formula [3] or the carboxylic acid anhydrides represented by the formula [4] is not particularly limited; however, it ranges normally from 0.1 to 5 moles, preferably from 0.2 to 3 moles and more preferably from 0.5 to 2 moles relative to 1 mole of 2-bromo-2,2-difluoroethanol. It is particularly preferable to use the carboxylic acid halides or the carboxylic acid anhydrides in an amount ranging from 0.8 to 1.5 moles.

The reaction may be conducted in the absence of solvents or may be conducted in a non-reactive solvent. Such solvents are required only to be non-reactive and not particularly limited. Hence the reaction may be conducted in, for example, water, an organic solvent, or a mixture of these. Examples of the organic solvent include: hydrocarbon-based solvents such as n-hexane, benzene and toluene; ketone-based solvents such as acetone, methyl ethyl ketone and methyl isobutyl ketone; ester-based solvents such as ethyl acetate and butyl acetate; ether-based solvents such as diethyl ether, diethylene glycol dimethyl ether, tetrahydrofuran and dioxane; halogen-based solvents such as dichloromethane, chloroform, carbon tetrachloride, 1,2-dichloroethane, tetrachloroethylene, chlorobenzene and ortho-chlorobenzene; and polar solvents such as acetonitrile, N,N-dimethylformamide, N,N-dimethylimidazolidinone, dimethyl sulfoxide and sulfolane. These solvents may be used singly or in combination of not less than two kinds thereof.

The reaction temperature is not particularly limited and normally within a range of from −78 to 150° C., preferably from −20 to 120° C. and more preferably from 0 to 100° C.

The reaction time depends on the reaction temperature; however, it ranges normally from several minutes to 100 hours, preferably from 30 minutes to 50 hours and more preferably from 1 to 20 hours. It is preferable that a temporal point at which the raw material 2-bromo-2,2-difluoroethanol is consumed is determined, by analytical devices such as gas chromatography (GC) and nuclear magnetic resonance (NMR), as the endpoint of the reaction.

In the case of using carboxylic acid halides represented by the formula [3], the reaction may be conducted in the absence of catalyst while removing hydrogen halides (e.g. hydrogen chloride) being produced as by-product from the reaction system or may be conducted with the use of a dehydrohalogenating agent (or an acid acceptor). Additionally, in the case of using carboxylic acid anhydrides represented by the formula [4], the reaction may be conducted with the use of an acid acceptor for receiving by-product acids.

Examples of the acid acceptor include: organic bases such as triethylamine, pyridine, picoline, dimethylaniline, diethylaniline, 1,4-diazabicyclo[2.2.2]octane (DABCO) and 1,8-diazabicyclo[5.4.0]undec-7-ene (DBU); and inorganic bases such as sodium hydrogencarbonate, sodium carbonate, potassium carbonate, lithium carbonate, sodium hydroxide, potassium hydroxide, calcium hydroxide and magnesium oxide. An amount of the acid acceptor to be used is not particularly limited but ranges from 0.05 to 10 moles, preferably from 0.1 to 5 moles and more preferably from 0.5 to 3 moles relative to 1 mole of 2-bromo-2,2-difluoroethanol.

Upon termination of the reaction, carboxylic acid bromodifluoroethyl ester represented by the formula [5] can be obtained by normal means including extraction, distillation, recrystallization and the like. Moreover, it can be purified by column chromatography, recrystallization or the like, as necessary.

Then, the 3rd step of the present invention will be now discussed. The 3rd step is a step of reacting carboxylic acid bromodifluoroethyl ester represented by the formula [5] and obtained in the 2nd step in the presence of a sulfinating agent thereby obtaining a 2-alkylcarbonyloxy-1,1-difluoroethane-sulfinic acid salt (a sulfination step).

The sulfinating agent that can be used in the present invention is represented by the formula [15].

[Chemical Formula 46]

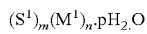

$(S^1)_m(M^1)_n \cdot pH_2O$       [15]

(in the above equation [15]: $S^1$ represents $S_2O_4$, $HOCH_2SO_2$, $SO_4$ or $HSO_4$; m and n represent an integer; p represents 0 (zero) or an integer; and $M^1$ represents Li, Na, K or $NH_4$.)

Concrete examples thereof are lithium dithionite, sodium dithionite, potassium dithionite, ammonium dithionite, lithium hydroxymethanesulfinate, sodium hydroxymethanesulfinate, lithium hydroxymethanesulfinate, potassium hydroxymethanesulfinate, ammonium hydroxymethanesulfinate, lithium sulfite, sodium sulfite, potassium sulfite, ammonium sulfite, lithium hydrogen sulfite sodium hydrogen sulfite, potassium hydrogen sulfite and ammonium hydrogen sulfite. Among these, sodium dithionite and potassium dithionite are preferable, and sodium dithionite is particularly preferable.

The molar ratio of the sulfinating agent to carboxylic acid bromodifluoroethyl ester [5] is normally from 0.5 to 10, preferably from 0.9 to 5.0 and particularly preferably 1.0 to 2.0.

Though this reaction can be conducted in air, the sulfinating agent is sometimes decomposed by water content in air. It is, therefore, preferable to conduct the reaction in an atmosphere of nitrogen or argon.

The reaction is accelerated with the addition of base, though sometimes developed without base. Therefore base is usually added thereto. Examples of the base to be added are lithium carbonate, sodium carbonate, potassium carbonate, lithium hydrogen carbonate, sodium hydrogencarbonate and potassium hydrogencarbonate, and preferably sodium hydrogencarbonate and potassium hydrogencarbonate.

This reaction is preferably conducted in a mixture solution of an organic solvent and water. Examples of the organic solvent are lower alcohols, tetrahydrofuran, N,N-dimethylformamide, N,N-dimethylacetamide, acetonitrile and dimethyl sulfoxide, and particularly preferably acetonitrile.

The ratio of the used organic solvent to 100 parts by weight of total of the organic solvent and water is normally not less than 5 parts by weight, preferably not less than 10 parts by weight, and more preferably within a range of from 20 to 90 parts by weight.

The reaction temperature is normally from 40 to 200° C., preferably from 60 to 100° C. The reaction time is normally from 0.5 to 120 hours, preferably from 2 to 72 hours; however, it is preferable that a temporal point at which the raw material carboxylic acid bromodifluoroethyl ester [5] is consumed is determined, by analytical devices such as thin layer chromatography (TLC) and nuclear magnetic resonance (NMR), as the endpoint of the reaction. If the carboxylic acid bromodifluoroethyl ester [5] is not consumed upon spending the reaction time, the reaction can be resumed by the further addition of water, the sulfinating agent and base upon separating a reaction solution into two layers and removing a water layer.

By the way, in the cases where a cation moiety of the sulfinating agent is identical with that of an inorganic base (e.g. "the case of using sodium dithionite as the sulfinating agent, and sodium carbonate as the inorganic base", "the case of using potassium sulfite as the sulfinating agent, and potassium hydrogencarbonate as the inorganic base" and the like), a 2-alkylcarbonyloxy-1,1-difluoroethanesulfinic acid salt represented by the formula [6] can be obtained as a single product.

[Chemical Formula 47]

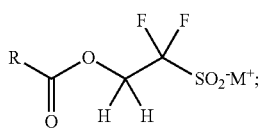

[6]

In such cases a further purification by recrystallization process or the like is possible, upon treating the reaction solution by concentration or the like.

If the cation moiety of the sulfinating agent and that of the inorganic base are not identical, the product is not single one in the strict definition but a mixture of cation derived from the sulfinating agent and that derived from the inorganic base, in the formula [6]. The ratio between the cations differs according to the ratio between the used sulfinating agent and the used inorganic base and to the reaction conditions. When the product is such a mixture, purification by using recrystallization or the like is in general difficult. To bring such a cation mixture to the next step as it is possible but makes analysis, purification and the like hard to be done. Therefore, when using the inorganic base as a base, it is preferable to use the sulfinating agent and the inorganic base whose cations are identical with each other.

Then, the 4th step of the present invention will be discussed. The 4th step is a step of reacting the 2-alkylcarbonyloxy-1,1-difluoroethanesulfinic acid salt [6] obtained in the 3rd step with an oxidizing agent thereby obtaining a 2-alkylcarbonyloxy-1,1-difluoroethanesulfonic acid salt represented by the formula [2] (an oxidation step).

An example of the oxidizing agent used in this step is hydrogen peroxide, and additionally m-chloroperbenzoic acid, t-butyl hydroperoxide, potassium peroxydisulfate, potassium permanganate, sodium perborate, m-sodium iodate, chromic acid, sodium dichromate, halogen, iodobenzene dichloride, iodobenzene diacetate, osmium (VIII) oxide, ruthenium (VIII) oxide, sodium hypochlorite, sodium chlorite, oxide gas and ozone gas, preferably hydrogen peroxide, m-chloroperbenzoic acid and t-butyl hydroperoxide.

The molar ratio of oxidizing agent to a 2-alkylcarbonyloxy-1,1-difluoroethanesulfinic acid salt [6] is normally from 0.9 to 10.0, preferably from 1.0 to 2.0. Sulfinic acid salts serving as the raw material are rough substances so that the exact number of moles may not be clear, in which case the oxidizing agent is preferably added relative to the molar amount of carboxylic acid bromodifluoroethyl ester represented by the formula [5].

Furthermore, the oxidizing agent can be used in combination with a transition metal catalyst. Examples of the transition metal catalyst are disodium tungstate, iron (III) chloride, ruthenium (III) chloride and selenium (IV) oxide, and preferably disodium tungstate.

The molar ratio of the transition metal catalyst to the 2-alkylcarbonyloxy-1,1-difluoroethanesulfinic acid salt is normally from 0.0001 to 1.0, preferably from 0.001 to 0.5, and more preferably from 0.001 to 0.1.

Moreover, in addition to the oxidizing agent and the transition metal catalyst, a buffer solution may be used for the purpose of adjusting the pH of the reaction solution. Examples of the buffer solution include disodium hydrogenphosphate, sodium dihydrogenphosphate, dipotassium hydrogenphosphate, and potassium dihydrogenphosphate. The molar ratio of the buffer solution to the 2-alkylcarbonyloxy-1,1-difluoroethanesulfinic acid salt is normally from 0.01 to 2.0, preferably from 0.03 to 1.0, more preferably from 0.05 to 0.5.

This reaction is usually conducted in a reaction solvent. Preferable examples of the reaction solvent are an organic solvent such as lower alcohols, tetrahydrofuran, N,N-dimethylformamide, N,N-dimethylacetamide, acetonitrile, dimethyl sulfoxide, acetic acid and trifluoroacetic acid, in addition to water. The more preferable are water, methanol, N,N-dimethylacetamide, acetonitrile and dimethyl sulfoxide. The particularly preferable are water and methanol.

Additionally, the organic solvent and water may be used in combination as necessary, in which case the ratio of the organic solvent to be used is normally not less than 5 parts by weight, preferably not less than 10 parts by weight, more preferably within a range of from 20 to 90 parts by weight relative to 100 parts by weight of total of the organic solvent and water. The amount of the reaction solvent to be used is normally from 1 to 100 parts by weight, preferably from 2 to 100 parts by weight, more preferably 5 to 50 parts by weight relative to 1 parts by weight of the 2-alkylcarbonyloxy-1,1-difluoroethanesulfinic acid salt.

The reaction temperature is usually from 0 to 100° C., preferably from 5 to 60° C. and more preferably from 5 to 40° C. The reaction time is usually from 0.1 to 72 hours, preferably from 0.5 to 24 hours and more preferably from 0.5 to 12 hours; however, it is preferable that a temporal point at which the raw material 2-alkylcarbonyloxy-1,1-difluoroethanesulfinic acid salt is consumed is determined, by analytical devices such as thin layer chromatography (TLC) and nuclear magnetic resonance (NMR), as the endpoint of the reaction.

Furthermore, the reaction solution can be brought to the next step as it is only with a treatment of such an extent as to conduct concentration, or can be purified by recrystallization or the like according to circumstances.

Then, the 5th step of the present invention will be discussed. The 5th step is a step of carrying out an onium-salt exchange on the 2-alkylcarbonyloxy-1,1-difluoroethanesulfonic acid salt represented by the formula [2] and obtained in the 4th step, by using a monovalent onium salt represented by the formula [7],

[Chemical Formula 48]

$$Q^+X^-$$ [7]

thereby obtaining a 2-alkylcarbonyloxy-1,1-difluoroethanesulfonic acid onium salt represented by the formula [8] (an onium-salt exchanging step 1).

Onium cation $Q^+$ included in the formula [7] is expressed with a sulfonium cation represented by the following formula (a) or (b), or an iodonium cation represented by the following formula (c).

[Chemical Formula 49]

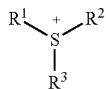
(a)

In the formula (a), $R^1$, $R^2$ and $R^3$ mutually independently represent a substituted or unsubstituted linear or branched alkyl group, alkenyl group or oxoalkyl group having 1 to 10 carbon atoms, or a substituted or unsubstituted aryl group, aralkyl group or aryloxoalkyl group having 6 to 18 carbon atoms. Furthermore, any two or more of $R^1$, $R^2$ and $R^3$ may bond to each other to form a ring together with a sulfur atom shown in the formula.

[Chemical Formula 50]

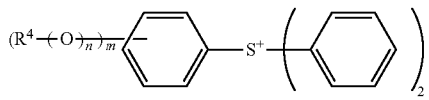
(b)

In the formula (b): $R^4$ represents a substituted or unsubstituted linear, branched or cyclic alkyl group or alkenyl group having 1 to 20 carbon atoms or a substituted or unsubstituted aryl group having 6 to 14 carbon atoms; m represents an integer of from 1 to 5; and n represents 0 (zero) or 1.

[Chemical Formula 51]

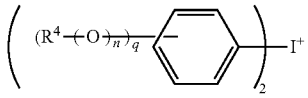
(c)

In the formula (c): $R^4$ represents a substituted or unsubstituted linear, branched or cyclic alkyl group or alkenyl group having 1 to 20 carbon atoms or a substituted or unsubstituted aryl group having 6 to 14 carbon atoms; q represents an integer of from 0 (zero) to 5; and n represents 0 (zero) or 1.

Hereinafter, a sulfonium cation represented by the formula (a) and the formula (b) and an iodonium cation represented by the formula (c) will be discussed in detail.

Sulfonium Cation Represented by the Formula (a)

Concrete examples of $R^1$, $R^2$ or $R^3$ as shown in the formula (a) are as follows. Examples of alkyl group include methyl group, ethyl group, n-propyl group, isopropyl group, cyclopropyl group, n-butyl group, sec-butyl group, isobutyl group, tert-butyl group, n-pentyl group, cyclopentyl group, n-hexyl group, n-heptyl group, 2-ethylhexyl group, cyclohexyl group, cycloheptyl group, 4-methylcyclohexyl group, cyclohexylmethyl group, n-octyl group, n-decyl group, 1-adamantyl group, 2-adamantyl group, bicyclo[2.2.1]hepten-2-yl group, 1-adamantanemethyl group and 2-adamantanemethyl group. Examples of alkenyl group include vinyl group, allyl group, propenyl group, butenyl group, hexenyl group and cyclohexenyl group. Examples of oxoalkyl group include 2-oxocyclopentyl group, 2-oxocyclohexyl group, 2-oxopropyl group, 2-cyclopentyl-2-oxoethyl group, 2-cyclohexyl-2-oxoethyl group and 2-(4-methylcyclohexyl)-2-oxoethyl group. Examples of aryl group are: phenyl group; naphthyl group; thienyl group; alkoxy phenyl groups such as p-methoxyphenyl group, m-methoxyphenyl group, o-methoxyphenyl group, p-ethoxyphenyl group, p-tert-butoxyphenyl group and m-tert-butoxyphenyl group; alkyl phenyl group such as 2-methylphenyl group, 3-methylphenyl group, 4-methylphenyl group and ethylphenyl group; alkyl naphthyl group such as methyl naphthyl group and ethyl naphthyl group; dialkyl naphthyl group such as diethyl naphthyl group; dialkoxy naphthyl group such as dimethoxy naphthyl group and diethoxy naphthyl group. Examples of aralkyl group include benzyl group, 1-phenylethyl group and 2-phenylethyl group. Examples of aryloxoalkyl group include 2-aryl-2-oxoethyl group such as 2-phenyl-2-oxoethyl group, 2-(1-naphthyl)-2-oxoethyl group and 2-(2-naphthyl)-2-oxoethyl group. Additionally, in the case where any two or more of $R^1$, $R^2$ and $R^3$ bond to each other through a sulfur atom to form a cyclic structure, the examples include 1,4-butylene and 3-oxa-1,5-pentylene. Examples of substituent are aryl groups having a polymerizable substituent such as acryloyloxy group and methacryloyloxy group, and more concretely include 4-(acryloyloxy)phenyl group, 4-(methacryloyloxy)phenyl group, 4-vinyloxyphenyl group and 4-vinylphenyl group.

Further concrete examples of sulfonium cation represented by the formula (a) include triphenylsulfonium, (4-tert-butylphenyl)diphenylsulfonium, bis(4-tert-butylphenyl)phenylsulfonium, tris(4-tert-butylphenyl)sulfonium, (3-tert-butylphenyl)diphenylsulfonium, bis(3-tert-butylphenyl)phenylsulfonium, tris(3-tert-butylphenyl)sulfonium, (3,4-ditert-butylphenyl)diphenylsulfonium, bis(3,4-ditert-butylphenyl)phenylsulfonium, tris(3,4-ditert-butylphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-ditert-butoxyphenyl)diphenylsulfonium, bis(3,4-ditert-butoxyphenyl)phenylsulfonium, tris(3,4-ditert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)diphenylsulfonium, (4-tert-butoxyphenyl)bis(4-dimethylaminophenyl)sulfonium, tris(4-dimethylaminophenyl)sulfonium, 2-naphthyldiphenylsulfonium, dimethyl(2-naphthyl)sulfonium, (4-hydroxyphenyl)dimethylsulfonium, (4-methoxyphenyl)dimethylsulfonium, trimethylsulfonium, (2-oxocyclohexyl)cyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, and 2-methoxynaphthyl-1-thiacyclopentanium. More preferable examples are triphenylsulfonium, (4-tert-butylphenyl)diphenylsulfonium, (4-tert-butoxyphenyl)diphenylsulfonium, tris(4-tert-butylphenyl)sulfonium and (4-tert-butoxycarbonylmethyloxyphenyl)diphenylsulfonium.

Still further examples thereof are 4-(methacryloyloxy)phenyldiphenylsulfonium, 4-(acryloyloxy)phenyldiphenylsulfonium, 4-(methacryloyloxy)phenyldimethylsulfonium, and 4-(acryloyloxy)phenyldimethylsulfonium. Regarding these polymerizable sulfonium cation, Japanese Patent Application Publication No. 4-230645, Japanese Patent Application Publication 2005-84365 and the like can be referred to.

Sulfonium Cation Represented by the Formula (b)

In the formula (b), $R^4$—$(O)_n$— group is not particularly limited in moiety at which $R^4$—$(O)_n$— group serves as a substituent, but preferably occupies position 4 or 3, more preferably position 4 of phenyl group. In the formula, n represents 0 (zero) or 1. Concrete examples of $R^4$ include methyl group, ethyl group, n-propyl group, sec-propyl group, cyclopropyl group, n-butyl group, sec-butyl group, isobutyl group, tert-butyl group, n-pentyl group, cyclopentyl group, n-hexyl group, cyclohexyl group, n-octyl group, n-decyl group, n-dodecyl group, 1-adamantyl group, 2-adamantyl group, bicyclo[2.2.1]hepten-2-yl group, phenyl group, 4-methoxyphenyl group, 4-tert-butylphenyl group, 4-biphenyl group, 1-naphthyl group, 2-naphthyl group, 10-anthranyl group and 2-furanyl group. In the case of n=1, the examples further include acryloyl group, methacryloyl group, vinyl group and allyl group.

Concrete examples of sulfonium cation are (4-methylphenyl)diphenylsulfonium, (4-ethylphenyl)diphenylsulfonium, (4-cyclohexylphenyl)diphenylsulfonium, (4-n-hexylphenyl)diphenylsulfonium, (4-n-octyl)phenyldiphenylsulfonium, (4-methoxyphenyl)diphenylsulfonium, (4-ethoxyphenyl)diphenylsulfonium, (4-tert-butoxyphenyl)diphenylsulfonium, (4-cyclohexyloxyphenyl)diphenylsulfonium, (4-trifluoromethylphenyl)diphenylsulfonium, (4-trifluoromethyloxyphenyl)diphenylsulfonium, and (4-tert-butoxycarbonylmethyloxyphenyl)diphenylsulfonium.

Iodonium Cation Represented by the Formula (c)

In the formula (c), $R^4$—$(O)_n$— group is not particularly limited in moiety at which $R^4$—$(O)_n$— group serves as a substituent, but preferably occupies position 4 or 3, more preferably position 4 of phenyl group. In the formula, n represents 0 (zero) or 1. Concrete examples of $R^4$ are the same as those discussed in the above formula (b).

Concrete examples of iodonium cation include diphenyliodonium, bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, (4-acryloyloxy)phenylphenyliodonium, and (4-methacryloyloxy)phenylphenyliodonium. Among these, bis(4-tert-butylphenyl)iodonium is preferably used.

Additionally, examples of a monovalent anion represented in the formula [7] by $X^-$ include $F^-$, $Cl^-$, $Br^-$, $I^-$, $ClO_4^-$, $HSO_4^-$, $H_2PO_4^-$, $BF_4^-$, $PF_6^-$, $SbF_6^-$, aliphatic sulfonic acid anion, aromatic sulfonic acid anion, trifluoromethanesulfonic acid anion, fluorosulfonic acid anion, aliphatic carboxylic acid anion, aromatic carboxylic acid anion, fluorocarboxylic acid anion and trifluoroacetic acid anion. The preferable are $Cl^-$, $Br^-$, $HSO_4^-$, $BF_4^-$, aliphatic sulfonic acid and the like. The more preferable are $Cl^-$, $Br^-$ and $HSO_4^-$.

The molar ratio of a monovalent onium salt represented in the formula [7] to a 2-alkylcarbonyloxy-1,1-difluoroethanesulfonic acid salt [2] (or [22]) is usually from 0.5 to 10.0, preferably from 0.8 to 2.0 and more preferably from 0.9 to 1.2.

This reaction is usually conducted in a reaction solvent. Preferable examples of the reaction solvent are an organic solvent such as lower alcohols, tetrahydrofuran, N,N-dimethylformamide, N,N-dimethylacetamide, acetonitrile and dimethyl sulfoxide, in addition to water. The more preferable are water, methanol, N,N-dimethylacetamide, acetonitrile and dimethyl sulfoxide. The particularly preferable is water.

Additionally, the organic solvent and water may be used in combination as necessary, in which case the ratio of the organic solvent to be used is normally not less than 5 parts by weight, preferably not less than 10 parts by weight, more preferably within a range of from 20 to 90 parts by weight relative to 100 parts by weight of total of the organic solvent and water. The amount of the reaction solvent to be used is normally from 1 to 100 parts by weight, preferably from 2 to 100 parts by weight, more preferably 5 to 50 parts by weight relative to 1 parts by weight of a counter ion exchange precursor.

The reaction temperature is usually from 0 to 80° C., preferably from 5 to 30° C. The reaction time is usually from 10 minutes to 16 hours, preferably from 30 minutes to 6 hours; however, it is preferable that a temporal point at which the raw material 2-alkylcarbonyloxy-1,1-difluoroethanesulfonic acid salt [2] (or [22]) is consumed is determined, by analytical devices such as thin layer chromatography (TLC) and nuclear magnetic resonance (NMR), as the endpoint of the reaction.

The thus obtained 2-alkylcarbonyloxy-1,1-difluoroethanesulfonic acid onium salt represented by the formula [8] can be rinsed with an organic solvent or can be extracted to be purified. Examples of the organic solvent are preferably those who are not to be mixed with water, including: esters such as ethyl acetate and n-butyl acetate; ethers such as diethyl ether; halogenated alkyls such as methylene chloride and chloroform.

By the process as had been discussed, a 2-alkylcarbonyloxy-1,1-difluoroethanesulfonic acid onium salt not having in its structure an unconjugated unsaturated moiety (a double or triple bond) as a substituent for acyl group. This compound can be provided as a photoacid generator used to a chemically amplified resist material. Those who have in its structure an unconjugated unsaturated moiety (a double or triple bond) as a substituent for acyl group are hard to be produced by the above steps so as to need to conduct further steps as below thereon.

Then, the 5'th step of the present invention will be discussed. The 5'th step is a step of saponifying (i.e. hydrolyzing in the presence of basic substance) the 2-alkylcarbonyloxy-1,1-difluoroethanesulfonic acid salt represented by the formula [2] and obtained in the 4th step thereby obtaining a 2-hydroxy-1,1-difluoroethanesulfonic acid salt represented by the formula [9] (a saponification step).

A process for saponifying a 2-alkylcarbonyloxy-1,1-difluoroethanesulfonic acid salt represented by the formula [2] is not particularly limited and therefore adopted from any of commonly known saponification processes. Examples thereof are as follows.

In general, saponification reaction is conducted in the presence of a basic catalyst in which hydroxide, bicarbonate and carbonate of one or more kinds of alkali metals, ammonia, amine compounds are included as a base. Examples of alkali metal compounds are sodium hydroxide, potassium hydroxide, lithium hydroxide, sodium hydrogencarbonate, potassium hydrogencarbonate, sodium carbonate and potassium carbonate. Examples of amine compounds are methylamine, dimethylamine, trimethylamine, ethylamine, diethylamine, triethylamine, propylamine, dipropylamine, tripropylamine, butylamine, dibutylamine, tributylamine, cyclohexylamine, benzylamine, morpholine, pyrrole, pyrrolidine, pyridine, ethanolamine, diethanolamine, triethanolamine, N,N-dimethylaminoethanol, N,N-diethylaminoethanol, ethylenediamine, diethylenetriamine, triethylenetetramine, 1,2-propylenediamine, dipropylenetriamine and tripropylenetetramine, and quaternary ammonium hydroxide salts of these.

The molar ratio of the base to a 2-alkylcarbonyloxy-1,1-difluoroethanesulfonic acid salt [2] is usually from 0.01 to 10.0, preferably from 0.1 to 5.0 and more preferably from 0.5 to 2.0.

This reaction is usually conducted in the presence of water. The molar ratio of water to a 2-alkylcarbonyloxy-1,1-difluoroethanesulfonic acid salt [2] is usually not less than 1 and has no upper limit. However, the molar ratio is preferably not more than 100 and more preferably not more than 50, since the use of an excessively large quantity of water reduces efficiency.

Additionally, water can be used in combination with an organic solvent as necessary, in which case the organic solvent to be used in combination are not particularly limited, but preferably those who can extract a 2-hydroxy-1,1-difluoroethanesulfonic acid salt represented by the formula [9] from a water layer. Examples of the organic solvent are preferably those who are not to be mixed with water, including: esters such as ethyl acetate and n-butyl acetate; ethers such as diethyl ether; and halogenated alkyls such as methylene chloride and chloroform.

In this case, the amount of the organic solvent is normally not less than 5 parts by weight, preferably not less than 10 parts by weight, more preferably within a range of from 20 to 90 parts by weight relative to 100 parts by weight of total of the organic solvents and water.

The reaction temperature is usually from 0 to 100° C., preferably from 5 to 80° C. The reaction time is usually from 10 minutes to 16 hours and preferably from 30 minutes to 6 hours; however, it is preferable that a temporal point at which the raw material 2-alkylcarbonyloxy-1,1-difluoroethanesulfonic acid salt [2] is consumed is determined, by analytical devices such as thin layer chromatography (TLC) and nuclear magnetic resonance (NMR), as the endpoint of the reaction.

The thus obtained 2-hydroxy-1,1-difluoroethanesulfonic acid salt represented by the formula [9] can be extracted with the organic solvent or purified by recrystallization, as necessary.

Then, the 6th step of the present invention will be discussed. The 6th step is a step of reacting the 2-hydroxy-1,1-difluoroethanesulfonic acid salt represented by the formula [9] with a carboxylic acid derivative represented by the formula [10] or the formula [11] to cause esterification, thereby producing a 2-alkylcarbonyloxy-1,1-difluoroethanesulfonic acid salt represented by the formula [12] ([a 6th step]: an esterification step 2).

Examples of R' shown in the formula [10] or the formula [11] are the same as those of R discussed above; however, R' is different from R in that its substituent may be exemplified further by linear, branched or cyclic alkenyl group. Concrete examples of alkenyl group are vinyl group, allyl group, 1-methylethenyl group, 1-methylallyl group, 2-methylallyl group, 1-propenyl group, isopropenyl group, 2-butenyl group, 3-butenyl group, 1,3-butadienyl group, 2-pentenyl group, 4-pentenyl group, 2-hexenyl group, 5-hexenyl group, cyclopropenyl group, cyclopentenyl group, cyclohexenyl group and 5-norbornen-1-yl group.

A 2-hydroxy-1,1-difluoroethanesulfonic acid salt [9] hardly dissolves in a hydrocarbon-based nonpolar solvent such as n-hexane, benzene and toluene so as not to be preferably used as the solvent used in this step. It is preferable to use: water; a ketone-based solvent such as methyl ethyl ketone and methyl isobutyl ketone; an ester-based solvent such as ethyl acetate and butyl acetate; an ether-based solvent such as diethyl ether, diethylene glycol dimethyl ether, tetrahydrofuran and dioxane; a halogen-based solvent such as dichloromethane, chloroform, carbon tetrachloride, 1,2-dichloroethane, tetrachloroethylene, chlorobenzene and ortho-chlorobenzene; and a polar solvent such as acetonitrile, N,N-dimethylformamide, N,N-dimethylimidazolidinone, dimethyl sulfoxide and sulfolane.

As discussed above, a 2-alkylcarbonyloxy-1,1-difluoroethanesulfonic acid salt represented by the formula [12] can be produced from a 2-hydroxy-1,1-difluoroethanesulfonic acid salt represented by the formula [9] by using: carboxylic acids or carboxylic acid halides represented by the formula [10] instead of carboxylic acids or carboxylic acid halides represented by the formula [3]; carboxylic acid anhydrides represented by the formula [11] instead of carboxylic acid anhydrides represented by the formula [4]; and the process generally similar to that in the 2nd step with the exception of slightly limiting the solvent to be used.

Upon termination of the reaction, a 2-alkylcarbonyloxy-1,1-difluoroethanesulfonic acid salt represented by the formula [12] can be obtained by normal means including extraction, solvent concentration and the like. Moreover, it can be purified by column chromatography, recrystallization or the like, as necessary.

Then, the 7th step of the present invention will be discussed. The 7th step is a step of carrying out an onium-salt exchange by using a monovalent onium salt represented by the formula [7] on the 2-alkylcarbonyloxy-1,1-difluoroethanesulfonic acid salt represented by the formula [12] and obtained in the 6th step, thereby obtaining a 2-hydroxy-1,1-difluoroethanesulfonic acid onium salt represented by the formula [13] (an onium-salt exchanging step 2). This step can be conducted in a similar manner to the 5th step (an onium-salt exchanging step 1).

By the way, the 6th step and the 7th step can be conducted in the reverse order (Equation [17]).

[Chemical Formula 52]

EQUATION [17]

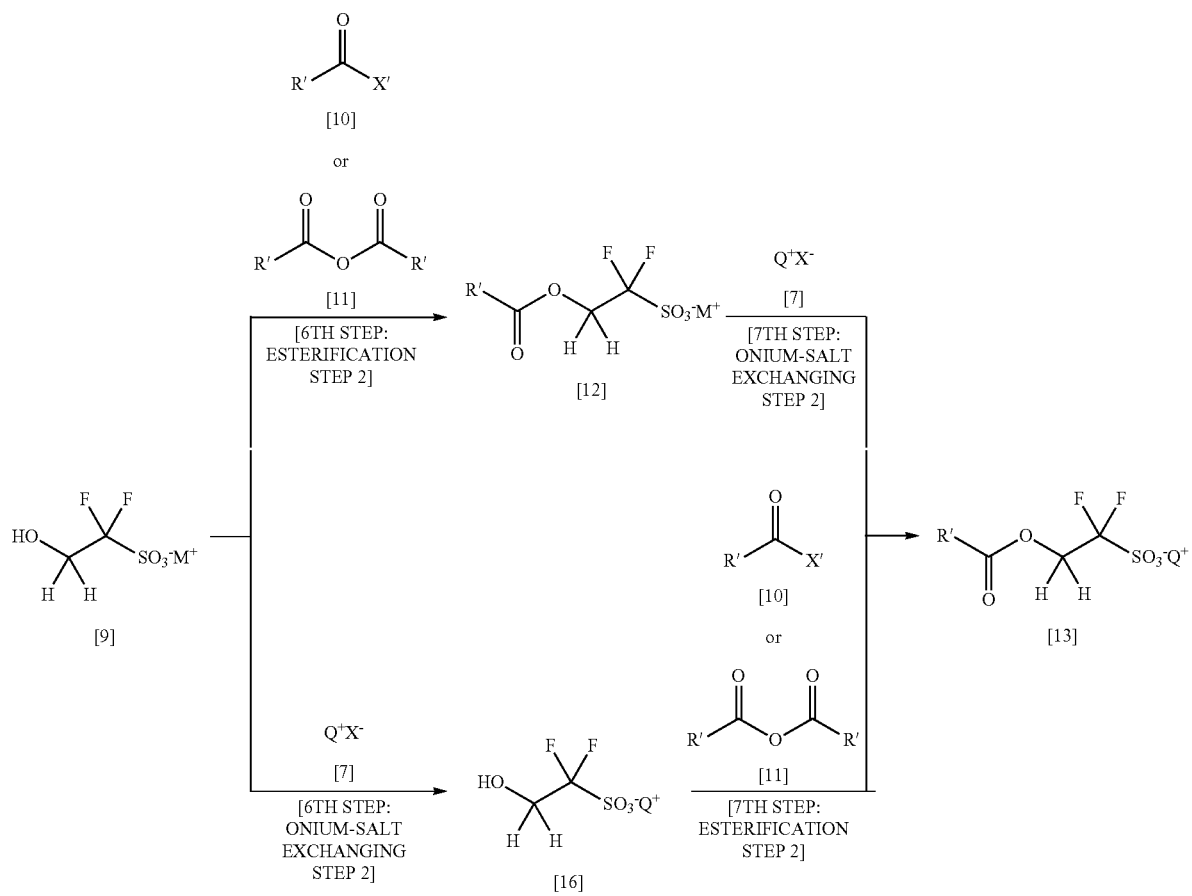

Namely, it is a process for carrying out an onium-salt exchange by using a monovalent onium salt represented by the formula [7] on a 2-hydroxy-1,1-difluoroethanesulfonic acid salt represented by the formula [9] to obtain a 2-hydroxy-1,1-difluoroethanesulfonic acid onium salt (a 6'th step: an onium-salt exchanging step 2), followed by esterification, thereby producing a 2-hydroxy-1,1-difluoroethanesulfonic acid onium salt represented by the formula [13] (a 7'th step: an esterification step 2).

This process, however, requires to use an enormously excessive amount of onium salt in the 6'th step, and additionally has had some disadvantages such as difficulty in purifying a 2-hydroxy-1,1-difluoroethanesulfonic acid onium salt represented by the formula [13] (Comparative Example 1).

Accordingly, it is a preferable process to conduct the 6th step and the 7th step in this order.

The present invention will be more specifically discussed with reference to the following Examples; however, the present invention is not limited by these Examples.

Example 1

[Production of 2-bromo-2,2-difluoroethanol] (a 1st Step: a Reduction Step)

A glass flask equipped with a thermometer, a condenser and a dropping funnel was charged with 186 g (4.91 moles) of sodium borohydride, 425 g (13.2 moles) of methanol and 3 L of diisopropyl ether, followed by stirring. Then, a diisopropyl ether solution (1 L) of 1000 g (4.92 moles) of ethyl bromodifluoroacetate was added thereto dropwise in an iced bath. After the termination of the dropping, stirring was conducted for 1 hour at room temperature. Then, the termination of the reaction was confirmed by gas chromatography. The reaction solution was separated into an organic layer and a water layer after the addition of 2.5 L of 2N hydrochloric acid, followed by extracting the water layer with 500 ml of diisopropyl ether. Subsequently, the organic layer was rinsed with 500 ml of saturated sodium hydrogencarbonate and 500 ml of saturated brine. Upon drying with anhydrous sodium sulfate, a solvent was distilled off and a precise distillation was performed, thereby obtaining 430 g (54% yield, 99% purity) of 2-bromo-2,2-difluoroethanol in the form of a colorless and transparent liquid.

Example 2

[Production of 2-bromo-2,2-difluoroethanol] (a 1st Step: a Reduction Step)

A glass flask equipped with a thermometer, a condenser and a dropping funnel was charged with 6 g (29.6 millimoles) of ethyl bromodifluoroacetate and 25 g of dehydrogenated diglyme, followed by stirring. Then, 1.5 g (39.5 millimoles) of lithium aluminohydride (LiAlH$_4$) was added thereto. It was heated to 60° C. and stirred for 12 hours, followed by cooling to room temperature, and then extraction was carried out thereon with the addition of diisopropyl ether and hydrochloric acid (1M). Upon separating into two layers, an organic layer was rinsed with saturated sodium bicarbonate water, saturated brine and water, followed by drying with magnesium sulfate. After filtration, a solvent was distilled off under a reduced pressure, thereby obtaining 3.8 g of the target 2-bromo-2,2-difluoroethanol (80% yield, 95% purity).

Example 3

[Production of 2-bromo-2,2-difluoroethanol] (a 1st Step: a Reduction Step)

A glass flask equipped with a thermometer, a condenser and a dropping funnel was charged with 27 g (140 millimoles) of ethyl bromodifluoroacetyl chloride and 200 g of tetrahydrofuran, followed by stirring. Then, 5.0 g (132 moles) of sodium borohydride (NaBH$_4$) was added thereto. It was heated to 60° C. and stirred for 16 hours, followed by cooling to room temperature, and then extraction was carried out thereon with the addition of diisopropyl ether and hydrochloric acid (1M). Upon separating into two layers, an organic layer was rinsed with saturated sodium bicarbonate water, saturated brine and water, followed by drying with magnesium sulfate. After filtration, a solvent was distilled off under a reduced pressure, thereby obtaining 19.2 g of the target 2-bromo-2,2-difluoroethanol (85% yield, 96% purity).

Example 4-1

[Production of 2-bromo-2,2-difluoroethyl pivalate] (a 2nd Step: Esterification Step)

[Chemical Formula 53]

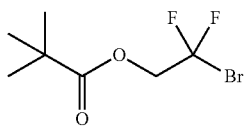

A glass flask equipped with a thermometer, a condenser and a dropping funnel was charged with 271 g (2.24 moles) of pivaloyl chloride, 360 g (2.23 moles) of 2-bromo-2,2-difluoroethanol and 1.5 L of diisopropyl ether, followed by stirring. Then, 318 g (3.14 moles) of triethylamine was added dropwise thereto, in an iced bath. After the termination of the dropping, stirring was conducted for 1 hour at room temperature. Then, the termination of the reaction was confirmed by gas chromatography. With the addition of 300 mL of water, a reaction solution was completely dissolved therein, followed by adding 500 mL of 2N hydrochloric acid thereto. The reaction solution was separated into an organic layer and a water layer, followed by extracting the water layer with 500 ml of diisopropyl ether. Subsequently, the organic layer was rinsed with 500 ml of saturated brine. Upon drying with anhydrous sodium sulfate, a solvent was distilled off, thereby obtaining 485 g (82% yield, 93% purity) of 2-bromo-2,2-difluoroethanol in the form of a light yellow liquid.

Properties of 2-bromo-2,2-difluoroethyl pivalate $^1$H NMR (Solvent for measurement: Deuterated chloroform, Reference material: Tetramethylsilane); δ=4.52 (t, 2H), 1.19 (s, 9H).

$^{19}$F NMR (Solvent for measurement: Deuterated chloroform, Reference material: Trichlorofluoromethane); δ=−56.6 (t, 2F).

Example 4-2

[Production of sodium 1,1-difluoro-2-(pivaloyloxy)ethanesulfinic acid] (a 3rd Step: a Sulfination Step)

[Chemical Formula 54]

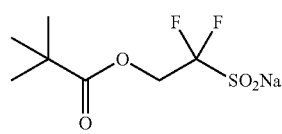

A glass flask equipped with a thermometer and a condenser was charged with 376 g (1.24 moles) of 2-bromo-2,2-difluoroethyl pivalate, 154 g (1.83 moles) of sodium hydrogencarbonate, 319 g (1.83 moles) of sodium dithionite, 1.2 L of acetonitrile and 1.2 L of water, followed by stirring for 4 hours at 70° C. It was cooled to room temperature and a water layer was eliminated therefrom. Thereafter 154 g (1.83 moles) of sodium hydrogencarbonate, 319 g (1.83 moles) of sodium dithionite and 1.2 L of water were added, followed by stirring for 4 hours at 70° C. This operation was further repeated two times. The termination of the reaction was confirmed by $^{19}$F NMR. An organic layer was separated from a reaction solution consisting of two layers and concentration and drying were conducted thereon, thereby obtaining 290 g of sodium 1,1-difluoro-2-(pivaloyloxy)ethanesulfinic acid in the form of a white solid (60% yield, 65% purity).

Properties of sodium 1,1-difluoro-2-(pivaloyloxy)ethanesulfinic acid $^1$H NMR (Solvent for measurement: Deuterated chloroform, Reference material: Tetramethylsilane); δ=4.41 (t, 2H), 1.14 (s, 9H).

$^{19}$F NMR (Solvent for measurement: Deuterated chloroform, Reference material: Trichlorofluoromethane); δ=−120.2 (t, 2F).

Example 4-3

[Production of sodium 1,1-difluoro-2-(pivaloyloxy)ethanesulfonate] (a 4th Step: an Oxidation Step)

[Chemical Formula 55]

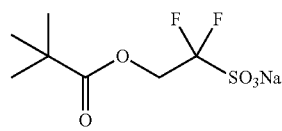

A glass flask equipped with a thermometer, a condenser and a dropping funnel was charged with 290 g (0.74 mole) of 65% purity sodium 1,1-difluoro-2-(pivaloyloxy)ethane-1-sulfinate, a catalytic amount of sodium tungstate (IV) dihydrate, 600 ml of water, followed by stirring. Then, 170 g (1.5 moles) of 30% oxygenate was added dropwise in an iced bath. After the termination of the dropping, stirring was conducted for 1 hour at room temperature. Then, the termination of the reaction was confirmed by $^{19}$F NMR. The reaction solution was concentrated and then rinsed with 500 ml of diisopropyl ether. Subsequently, filtration was conducted and a solid obtained therewith was dried, thereby obtaining 278 g of sodium 1,1-difluoro-2-(pivaloyloxy)ethanesulfonate in the form of a white solid (91% yield, 65% purity).

Properties of sodium
1,1-difluoro-2-(pivaloyloxy)ethanesulfonate $^1$H NMR (Solvent for measurement: Deuterated chloroform, Reference material: Tetramethylsilane); δ=4.52 (t, 2H), 1.15 (s, 9H).

$^{19}$F NMR (Solvent for measurement: Deuterated chloroform, Reference material: Trichlorofluoromethane); δ=–113.8 (t, 2F).

Example 5-1

[Production of 2-bromo-2,2,-difluoroethyl valerate]
(a 2nd Step: an Esterification Step 1)

[Chemical Formula 56]

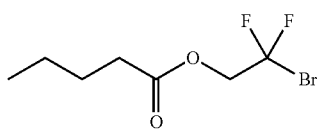

A 200 mL reactor was charged under nitrogen with 6.0 g (50.0 millimoles) of valeryl chloride and 90 mL of THF (dehydrated) and then put into an iced bath, to which 11.3 g (93% purity, 65.3 millimoles/1.31 equivalents) of 2-bromo-2,2,-difluoroethanol was added and then 7.1 g (70.0 millimoles/1.4 equivalents) of triethylamine was added dropwise. After the dropping, stirring was conducted at room temperature for 18 hours. Thereafter 35 ml of water was added thereto and extraction was carried out two times with 100 mL of diisopropyl ether. The obtained organic layer was further rinsed with diluted hydrochloric acid, sodium bicarbonate water and brine. Then, water content was eliminated with sodium sulfate, followed by filtration. Upon this, isopropyl ether was distilled off thereby obtaining 9.9 g of the target (2-bromo-2,2,-difluoro)ethyl valerate. In this case, purity was 89% and yield was 72%.

Properties of (2-bromo-2,2,-difluoro)ethyl valerate $^1$H NMR (Solvent for measurement: Deuterated chloroform, Reference material: Tetramethylsilane); δ=4.53 (t, J=11.6 Hz, 2H; CH$_2$), 2.36 (t, J=7.6 Hz, 2H; CH$_2$), 1.59 (quintet, J=7.6 Hz, 2H; CH$_2$), 1.31 (sextet, J=7.6 Hz, 2H; CH$_2$), 0.86 (t, J=7.6 Hz, 3H; CH$_3$).

$^{19}$F NMR (Solvent for measurement: Deuterated chloroform, Reference material: Trichlorofluoromethane); δ=–56.74 (t, J=11.6 Hz, 2F; CF$_2$).

Example 5-2

[Production of sodium
1,1-difluoro-2-(valeryloxy)ethanesulfinate] (a 3rd
Step: a Sulfination Step)

[Chemical Formula 57]

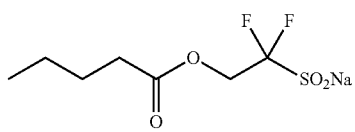

A 200 mL reactor was charged under nitrogen with 9.7 g (89% purity, 35.4 millimoles) of (2-bromo-2,2,-difluoro) ethyl valerate, 40 g of acetonitrile, 5.9 g (70.7 millimoles/2.0 equivalents) of sodium hydrogencarbonate, 8.7 g (50.1 millimoles/1.5 equivalents) of sodium dithionite and 40 g of water, followed by stirring at 60° C. for 1.5 hours and at 80° C. for 16 hours. The reactor was further charged with 5.9 g (70.7 millimoles) of sodium hydrogencarbonate and 8.7 g (50.1 millimoles) of sodium dithionite, followed by stirring at 80° C. for 94 hours. Extraction was conducted on a reaction solution six times with 40 mL of acetonitrile and then a solvent was distilled out of the obtained organic layer, followed by rinsing with 200 mL of diisopropyl ether. Then, filtration was conducted thereon, followed by drying a solid, thereby obtaining 6.74 g of the target sodium 2-valeryloxy-1,1-difluoroethanesulfinate. In this case, purity was 28% and yield was 21%.

Properties of sodium
2-valeryloxy-1,1-difluoroethanesulfinate $^1$H NMR (Solvent for measurement: Deuterated chloroform, Reference material: Tetramethylsilane); δ=4.42 (t, J=16.4 Hz, 2H; CH$_2$), 2.34 (t, J=7.6 Hz, 2H; CH$_2$), 1.50 (quintet, J=7.6 Hz, 2H; CH$_2$), 1.28 (sextet, J=7.6 Hz, 2H; CH$_2$), 0.85 (t, J=7.6 Hz, 3H; CH$_3$).

$^{19}$F NMR (Solvent for measurement: Deuterated chloroform, Reference material: Trichlorofluoromethane); δ=–119.95 (t, J=16.4 Hz, 2F; CF$_2$).

Example 5-3

[Production of sodium
1,1-difluoro-2-(valeryloxy)ethanesulfonate] (a 4th
Step: an Oxidation Step)

[Chemical Formula 58]

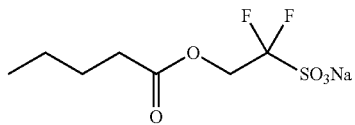

A 100 mL reactor was charged with 6.6 g (28% purity, 7.3 millimoles) of sodium 2-valeryloxy-1,1-difluoroethanesulfinate, 60 mL of water, 0.0047 g (0.014 millimole/0.0019 equivalent) of disodium tungstate dihydrate and 1.9 g (16.4 millimoles/2.25 equivalents) of 30% oxygenate, followed by stirring at room temperature for 1.5 hours. A reaction solution was heated under a reduced pressure to evaporate a volatile component to dryness, thereby obtaining 6.6 g of the target sodium 2-valeryloxy-1,1-difluoroethane sulfonate. In this case, purity was 26% and yield was 88%.

Properties of sodium 2-valeryloxy-1,1-difluoroethane sulfonate $^{1}$H NMR (Solvent for measurement: Deuterated DMSO, Reference material: Tetramethylsilane); δ=4.52 (t, J=15.6 Hz, 2H; CH$_2$), 2.34 (t, J=7.6 Hz, 2H; CH$_2$), 1.51 (quintet, J=7.6 Hz, 2H; CH$_2$), 1.28 (sextet, J=7.6 Hz, 2H; CH$_2$), 0.85 (t, J=7.6 Hz, 3H; CH$_3$).

$^{19}$F NMR (Solvent for measurement: Deuterated DMSO, Reference material: Trichlorofluoromethane); δ=−113.70 (t, J=15.6 Hz, 2F; CF$_2$).

Example 6-1

[Production of 2'-bromo-2',2'-difluoroethyl 1-adamantanecarboxylate] (a 2nd Step: an Esterification Step 1)

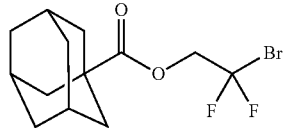

[Chemical Formula 59]

A 300 mL reactor was charged under nitrogen with 14.2 g (71.3 millimoles) of 1-adamantanecarbonyl chloride and 120 mL of THF (dehydrated), followed by putting it in an iced bath. There 16.1 g (92% purity, 91.8 millimoles/1.29 equivalents) of 2-bromo-2,2-difluoroethanol was added, and 10.1 g (99.8 millimoles/1.4 equivalents) of triethylamine was added dropwise. After the dropping, stirring was conducted at 60° C. for 23 hours. Then, 50 mL of water was added, and extraction was conducted two times with 150 mL of diisopropyl ether. The obtained organic layer was further rinsed with diluted hydrochloric acid, sodium bicarbonate water and brine, followed by removing water content with sodium sulfate, filtration, and then distilling isopropyl ether off, thereby obtaining 23.2 g of the target 2'-bromo-2',2'-difluoroethyl 1-adamantanecarboxylate. In this case, purity was 85%, and yield was 86%.

Properties of 2'-bromo-2',2'-difluoroethyl 1-adamantanecarboxylate $^{1}$H NMR (Solvent for measurement: Deuterated chloroform, Reference material: Tetramethylsilane); δ=4.51 (t, J=11.6 Hz, 2H; CH$_2$), 1.97 (m, 3H; 1-Ad), 1.87 (m, 6H; 1-Ad), 1.66 (m, 6H; 1-Ad).

$^{19}$F NMR (Solvent for measurement: Deuterated chloroform, Reference material: Trichlorofluoromethane); δ=−56.46 (t, J=11.6 Hz, 2F; CF$_2$).

Example 6-2

[Production of sodium 2-(1'-adamantane)carbonyloxy-1,1-difluoroethanesulfinate] (a 3rd Step: a Sulfination Step)

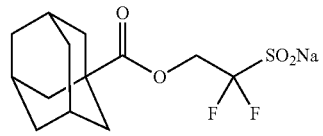

[Chemical Formula 60]

A 300 mL vessel was charged under nitrogen with 22.8 g (85% purity, 60.0 millimoles) of 2'-bromo-2',2'-difluoroethyl 1-adamantanecarboxylate, 80 g of acetonitrile, 10.1 g (120 millimoles/2.0 equivalents) of sodium hydrogencarbonate, 15.7 g (90.0 millimoles/1.5 equivalents) of sodium dithionite and 80 g of water, followed by stirring at 70° C. for 66 hours. The reactor was further charged with 6.7 g (80.0 millimoles) of sodium hydrogencarbonate and 10.5 g (60.0 millimoles) of sodium dithionite, followed by stirring at 80° C. for 24 hours. Extraction was conducted on a reaction solution one time with 30 mL of acetonitrile and then a solvent was distilled out of the obtained organic layer, followed by rinsing with 400 mL of diisopropyl ether. Then, filtration was conducted thereon, followed by drying a solid, thereby obtaining 12.0 g of the target sodium 2-(1'-adamantane)carbonyloxy-1,1-difluoroethanesulfinate. In this case, purity was 65%. Furthermore, the solvent was distilled out of a rinsing liquid thereby recovering 11.3 g of (2'-bromo-2',2'-difluoro)ethyl 1-adamantanecarboxylate. In this case purity was 71%.

A 200 mL vessel was charged under nitrogen with 11.1 g (71% purity, 24.4 millimoles) of the recovered (2'-bromo-2', 2'-difluoro)ethyl 1-adamantanecarboxylate, 40 g of acetonitrile, 4.1 g (48.8 millimoles/2.0 equivalents) of sodium hydrogencarbonate, 6.4 g (36.6 millimoles/1.5 equivalents) of sodium dithionite and 40 g of water, followed by stirring at 80° C. for 18 hours. The reactor was further charged with 1.9 g (22.4 millimoles) of sodium hydrogencarbonate and 2.9 g (16.8 millimoles) of sodium dithionite, followed by stirring at 80° C. for 22 hours. Extraction was conducted on a reaction solution one time with 30 mL of acetonitrile and then a solvent was distilled out of the obtained organic layer, followed by rinsing with 250 mL of diisopropyl ether. Then, filtration was conducted thereon, followed by drying a solid, thereby obtaining 6.9 g of the target sodium 2-(1'-adamantane)carbonyloxy-1,1-difluoroethanesulfinate. In this case, purity was 61%.

Properties of sodium 2-(1'-adamantane)carbonyloxy-1,1-difluoroethanesulfinate $^{1}$H NMR (Solvent for measurement: Deuterated DMSO, Reference material: Tetramethylsilane); δ=4.42 (t, J=16.4 Hz, 2H; CH$_2$), 1.93 (m, 3H; 1-Ad), 1.80 (m, 6H; 1-Ad), 1.63 (m, 6H; 1-Ad).

$^{19}$F NMR (Solvent for measurement: Deuterated DMSO, Reference material: Trichlorofluoromethane); δ=−120.23 (t, J=16.4 Hz, 2F; CF$_2$).

Example 6-3

[Production of sodium 2-(1'-adamantane)carbonyloxy-1,1-difluoroethanesulfonate] (a 4th Step: an Oxidation Step)

[Chemical Formula 61]

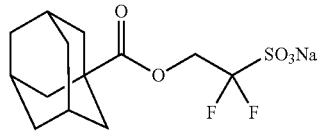

A 300 mL reactor was charged with 18.6 g (64% purity, 36.0 millimoles) of sodium 2-(1'-adamantane)carbonyloxy-1,1-difluoroethanesulfinate, 120 mL of water, 0.0154 g (0.047 millimole/0.0013 equivalent) of disodium tungstate dihydrate and 6.1 g (53.9 millimoles/1.5 equivalents) of 30% oxygenate, followed by stirring at room temperature for 2 hours. A reaction solution was heated under a reduced pressure to evaporate a volatile component to dryness, thereby obtaining 18.6 g of the target sodium 2-(1'-adamantane)carbonyloxy-1,1-difluoroethanesulfonate. In this case, purity was 65% and yield was 97%.

Properties of sodium 2-(1'-adamantane)carbonyloxy-1,1-difluoroethanesulfonate $^1$H NMR (Solvent for measurement: Deuterated DMSO, Reference material: Tetramethylsilane); δ=4.51 (t, J=15.3 Hz, 2H; CH$_2$), 1.96 (m, 3H; 1-Ad), 1.82 (m, 6H; 1-Ad), 1.65 (m, 6H; 1-Ad).
$^{19}$F NMR (Solvent for measurement: Deuterated DMSO, Reference material: Trichlorofluoromethane); δ=−113.94 (t, J=16.4 Hz, 2F; CF$_2$).

Example 7

[Production of triphenylsulfonium 1,1-difluoro-2-(valeryloxy)ethanesulfonate] (a 5th Step: an Onium-Salt Exchanging Step 1)

[Chemical Formula 62]

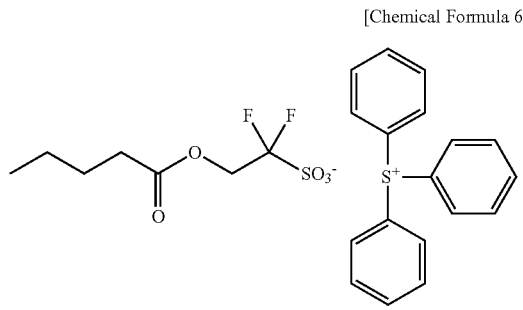

A 100 mL reactor was charged with 3.0 g (26% purity, 2.9 millimoles) of sodium 1,1-difluoro-2-(valeryloxy)ethanesulfonate obtained in Example 5-3 and 30 g of water, followed by adding dropwise an aqueous solution of triphenylsulfonium chloride [17.8 g (5.2 millimoles/1.8 equivalents) of triphenylsulfonium chloride and 16.2 g of water] at room temperature, followed by stirring at room temperature for 1.5 hours. Then, extraction was conducted by adding 30 mL of chloroform. The obtained organic layer was rinsed two times with water, followed by distilling a solvent off, thereby obtaining 0.96 g of the target triphenylsulfonium 1,1-difluoro-2-(valeryloxy)ethanesulfonate.

In this case, purity was 98%, and yield was 64%.

Properties of triphenylsulfonium 1,1-difluoro-2-(valeryloxy)ethanesulfonate $^1$H NMR (Solvent for measurement: Deuterated DMSO, Reference material: Tetramethylsilane); δ=7.92-7.70 (m, 15H, Ph$_3$S$^+$), 4.52 (t, J=15.6 Hz, 2H; CH$_2$), 2.36 (t, J=7.2 Hz, 2H; CH$_2$), 1.49 (quintet, J=7.2 Hz, 2H; CH$_2$), 1.28 (sextet, J=7.2 Hz, 2H; CH$_2$), 0.85 (t, J=7.2 Hz, 3H; CH$_3$).
$^{19}$F NMR (Solvent for measurement: Deuterated DMSO, Reference material: Trichlorofluoromethane); δ=−113.72 (t, J=15.6 Hz, 2F; CF$_2$).

Example 8

[Production of triphenylsulfonium 2-(1'-adamantane)carbonyloxy-1,1-difluoroethanesulfonate] (a 5th Step: an Onium-Salt Exchanging Step 1)

[Chemical Formula 63]

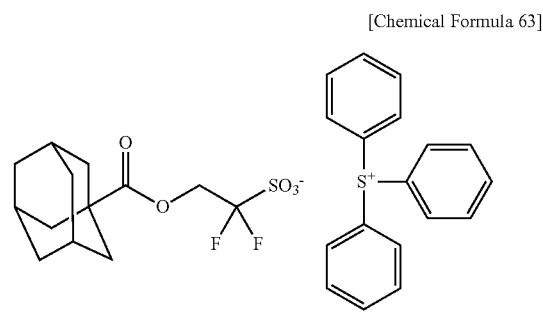

A 200 mL reactor was charged with 9.5 g (65% purity, 17.8 millimoles) of sodium 2-(1'-adamantane)carbonyloxy-1,1-difluoroethanesulfonate obtained in Example 6-3 and 85 g of water, followed by adding dropwise an aqueous solution of triphenylsulfonium chloride [5.6 g (19.6 millimoles/1.1 equivalents) of triphenylsulfonium chloride and 61.7 g of water] at room temperature, followed by stirring at room temperature for 1.5 hours. Then, filtration was conducted and then a solid was dried, thereby obtaining 9.8 g of the target triphenylsulfonium 2-(1'-adamantane)carbonyloxy-1,1-difluoroethanesulfonate. In this case, purity was 98% and yield was 92%.

Properties of triphenylsulfonium 2-(1'-adamantane)carbonyloxy-1,1-difluoroethanesulfonate $^1$H NMR (Solvent for measurement: Deuterated DMSO, Reference material: Tetramethylsilane); δ=7.91-7.72 (m, 15H, Ph$_3$S$^+$), 4.51 (t, J=15.3 Hz, 2H; CH$_2$), 1.96 (m, 3H; 1-Ad), 1.82 (m, 6H; 1-Ad), 1.65 (m, 6H; 1-Ad).

$^{19}$F NMR (Solvent for measurement: Deuterated DMSO, Reference material: Trichlorofluoromethane); δ=−113.97 (t, J=15.3 Hz, 2F; CF$_2$).

Example 9-1

[Production of sodium 2-hydroxy-1,1-difluoroethanesulfonate] (a 5'th Step: a Saponification Step)

[Chemical Formula 64]

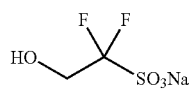

A 2 L reactor was charged with 180.0 g (57% purity, 0.38 mole) of sodium 1,1-difluoro-2-(pivaloyloxy)ethanesulfonate obtained by the same method as that in Example 4-3, 500 mL of water and 95.8 g (1.15 moles/3 equivalents) of 48% sodium hydroxide aqueous solution, followed by stirring at room temperature for 1.5 hours. There, 151.0 g (1.53 moles/4 equivalents) of 37% hydrochloric acid aqueous solution was added, followed by stirring at room temperature for 1 hour and rinsing two times with 250 mL of diisopropyl ether. Then, a solvent was distilled out of the obtained water layer, thereby obtaining 183.7 g of the target sodium 2-hydroxy-1,1-difluoroethanesulfonate. In this case, purity was 38%, and yield was 99%.

Properties of sodium 2-hydroxy-1,1-difluoroethanesulfonate $^1$H NMR (Solvent for measurement: Deuterated DMSO, Reference material: Tetramethylsilane); δ=3.80 (t, J=16.0 Hz, 2H; CH$_2$).
$^{19}$F NMR (Solvent for measurement: Deuterated DMSO, Reference material: Trichlorofluoromethane); δ=−115.34 (t, J=16.0 Hz, 2F; CF$_2$).

Example 9-2

[Production of sodium 1,1-difluoro-2-(2-methacryloyloxy)-ethanesulfonate] (a 6th Step: an Esterification Step 2)

[Chemical Formula 65]

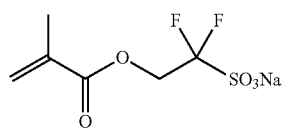

A 10 L reactor was charged with 562.0 g (39% purity, 1.19 moles) of sodium 2-hydroxy-1,1-difluoroethanesulfonate, 3 kg of acetonitrile, 40 mg of nonflex MBP and 367.0 g (2.38 moles/2.0 equivalents) of methacrylic anhydride in this order, followed by putting it into an iced bath. There, 361.0 g (3.57 moles/3.0 equivalents) of triethylamine was added dropwise. After the dropping, stirring was conducted at room temperature for 5 hours. Thereafter, 1.6 L of water was added and then acetonitrile was distilled off. The obtained water layer was rinsed two times with 0.5 L of isopropyl ether, thereby obtaining 288.0 g of the target sodium 1,1-difluoro-2-(2-methacryloyloxy)-ethanesulfonate (10 wt % aqueous solution). In this case, yield was 96%.

Properties of sodium 1,1-difluoro-2-(2-methacryloyloxy)-ethane sulfonate $^1$H NMR (Solvent for measurement: Deuterated DMSO, Reference material: Tetramethylsilane); δ=5.91 (s, 1H), 5.52 (s, 1H), 4.61 (t, J=16.0 Hz, 2H; CH$_2$), 1.81 (s, 3H).
$^{19}$F NMR (Solvent for measurement: Deuterated DMSO, Reference material: Trichlorofluoromethane); δ=−113.68 (t, J=16.0 Hz, 2F; CF$_2$).

Example 9-3

[Production of triphenylsulfonium 1,1-difluoro-2-(2-methacryloyloxy)-ethanesulfonate] (a 7th Step: an Onium-Salt Exchanging Step 2)

[Chemical Formula 66]

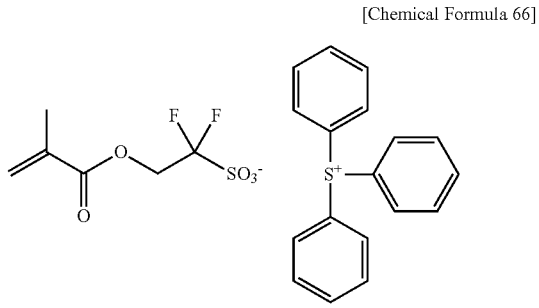

A 5 L reactor was charged with 288.0 g of sodium 1,1-difluoro-2-(2-methacryloyloxy)-ethanesulfonate (10 wt % aqueous solution) obtained in Example 9-2, 0.8 kg of chloroform and 40 mg of nonflex MBP. There, an aqueous solution of triphenylsulfonium chloride [409 g (1.37 moles/1.2 equivalents) of triphenylsulfonium chloride and 800 g of water] was added dropwise at room temperature, followed by stirring at room temperature for 1.5 hours. Thereafter it was separated into a water layer and a chloroform layer. The obtained chloroform layer was rinsed one time with 2N HCl and six times with water, followed by distilling chloroform off. There, 1.1 kg of methyl ethyl ketone and 0.3 kg of hexane were added, followed by filtration and preparing a methyl ethyl ketone/hexane mixture solution. On the other hand, a 5 L reactor charged with 2 L of hexane was prepared, to which the prepared methyl ethyl ketone/hexane mixture solution was added dropwise at room temperature while stirring. After the dropping, stirring was conducted at room temperature for 1 hour. The precipitated solid was separated by filtration and then dried, thereby obtaining 562 g of the target triphenylsulfonium 1,1-difluoro-2-(2-methacryloyloxy)-ethanesulfonate. In this case, purity was 98%, and yield was 98%.

Properties of triphenylsulfonium 1,1-difluoro-2-(2-methacryloyloxy)-ethanesulfonate $^1$H NMR (Solvent for measurement: Deuterated DMSO, Reference material: Tetramethylsilane); δ=7.92-7.65 (m, 15H, Ph$_3$S$^+$), 6.19 (s, 1H), 5.57 (s, 1H), 4.81 (t, J=16.0 Hz, 2H; CH$_2$), 1.92 (s, 3H).

$^{19}$F NMR (Solvent for measurement: Deuterated DMSO, Reference material: Trichlorofluoromethane); δ=−114.49 (t, J=16.0 Hz, 2F; CF$_2$).

Comparative Example 1

[Chemical Formula 67]

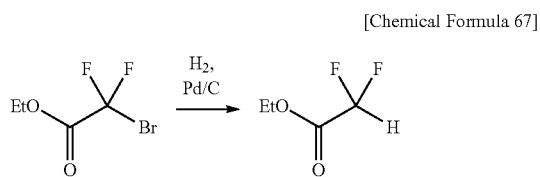

A 30 ml autoclave formed of stainless steel was charged with 2.35 g (11.6 millimoles) of ethyl 2-bromo-2,2-difluoroacetate, 12 ml of methanol and 100 mg of an activated carbon-carrying palladium catalyst (metal-carrying amount: 5%, water content: 46%), followed by causing a reaction at 40° C. for 2 hours under 1 MPa of hydrogen pressure. A reaction solution was analyzed by using gas chromatography, by which there were detected 32% of ethyl 2-bromo-2,2-difluoroacetate and 66% of ethyl 2,2-difluoroacetate which were remained unreacted. The target 2-bromo-2,2-difluoroethanol produced was only a little under 2%.

Comparative Example 2

[Chemical Formula 68]

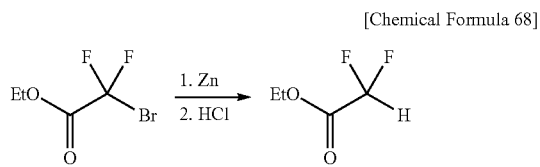

Under a nitrogen atmosphere, a suspension formed containing 6.0 g (88.5 millimoles) of active zinc and 50 ml of tetrahydrofuran was slowly added dropwise to a solution formed containing 9.0 g (44.3 millimoles) of ethyl 2-bromo-2,2-difluoroacetate and 50 ml of tetrahydrofuran at room temperature. Thereafter it was heated at 50° C. for 1 hour and then cooled to 0° C. Subsequently, 1M hydrochloric acid was added thereto, followed by extraction with diisopropyl ether. The obtained organic layer was rinsed with saturated sodium bicarbonate, saturated brine and water, followed by drying with magnesium sulfate. The organic layer was analyzed by gas chromatography, with which about 90% of ethyl 2,2-difluoroacetate was detected as the principal product. The target 2-bromo-2,2-difluoroethanol was produced little.

Comparative Example 3

[Chemical Formula 69]

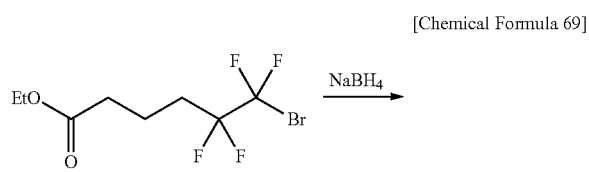

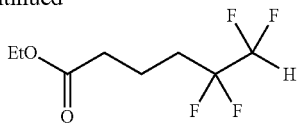

Under a nitrogen atmosphere, 1 g (3.39 millimoles) of ethyl 6-bromo-5,5,6,6-tetrafluorohexanoate was dissolved in 10 mL of tetrahydrofuran and 1 mL of methanol and then 129 mg (3.39 millimoles) of sodium borohydride was added thereto, followed by stirring at room temperature for 1 hour. A reaction solution was extracted with ethyl acetate after the addition of a sulfuric acid aqueous solution, followed by concentrating a solvent. With this, ethyl 5,5,6,6-tetrafluorohexanoate was obtained at a yield of 50%. There cannot be confirmed production of 6-bromo-5,5,6,6-tetrafluorohexan-1-ol.

Comparative Example 4

[Chemical Formula 70]

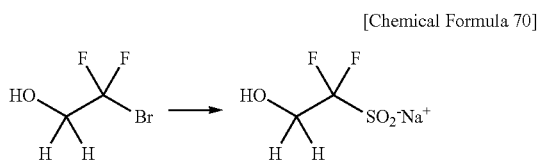

To a solution formed containing 8.92 g (55.4 millimoles) of 2-bromo-2,2-difluoroethanol, 12 g of acetonitrile and 22 g of water, 5.43 g (64.6 millimoles) of sodium hydrogencarbonate and 9.69 g (55.6 millimoles) of sodium dithionite were added. The solution separated into two layers was stirred at 60° C. for 12 hours, followed by cooling to room temperature. Thereafter, a solvent (an organic and a water layer) was distilled off under a reduced pressure and then dried, thereby obtaining 7.0 g of a white solid. The solid was analyzed by nuclear magnetic resonance (NMR), in which the content of the target sodium 1,1-difluoro-2-hydroxyethanesulfinate was about 8% and the yield obtained by conversion based thereon was 6%.

Comparative Example 5

[Chemical Formula 71]

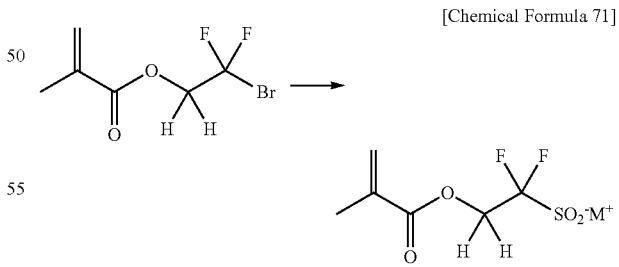

A glass flask equipped with a thermometer and a condenser was charged with 5 g (21.8 millimoles) of 2-bromo-2,2-difluoroethyl(2-methylacrylate), 40 g of acetonitrile and 40 g of water, followed by stirring. The flask was further charged with 2.2 g (26.2 millimoles) of sodium hydrogencarbonate and 5.7 g (32.7 millimoles) of sodium dithionite, followed by stirring for 2 hours at 60° C. An organic layer of a reaction solution was analyzed by using nuclear magnetic resonance (NMR), by which there was not detected the target sodium 1,1-difluoro-2-(2-methacryloyloxy)-ethanesulfinate but detected generally only a by-product formed from decomposed methacryl moiety.

Comparative Example 6

[Chemical Formula 72]

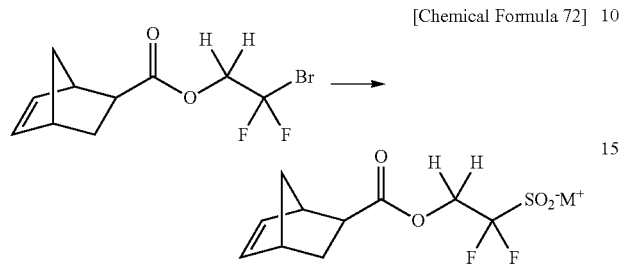

A glass flask equipped with a thermometer and a condenser was charged with 6.13 g (21.8 millimoles) of 5-norbornene-2-carboxylic acid 2-bromo-2,2-difluoroethyl ester, 40 g of acetonitrile and 40 g of water, followed by stirring. The flask was further charged with 2.2 g (26.2 millimoles) of sodium hydrogencarbonate and 5.7 g (32.7 millimoles) of sodium dithionite, followed by stirring for 1 hour at 65° C. An organic layer of a reaction solution was analyzed by using nuclear magnetic resonance (NMR), by which there was not detected the target sulfinic acid salt but detected generally only a by-product having such a moiety as to lose a double bond.

Comparative Example 7-1

[Production of triphenylsulfonium 2-hydroxy-1,1-difluoroethanesulfonate] (a 6'th Step: an Onium-Salt Exchanging Step 2)

[Chemical Formula 73]

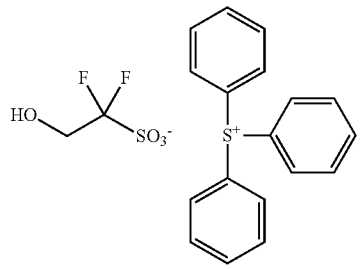

A 2 L reactor was charged with 183.7 g (38% purity, 0.38 mole) of sodium 2-hydroxy-1,1-difluoroethanesulfonate, 300 mL of water, 450 mL of chloroform and an aqueous solution of triphenylsulfonium chloride [142.8 g (0.49 mole/1.25 equivalents) of triphenylsulfonium chloride and 150 mL of water], followed by stirring at room temperature for 1 hour. A reaction solution was analyzed by using nuclear magnetic resonance (NMR), by which there was found almost half raw material sodium 2-hydroxy-1,1-difluoroethanesulfonate remaining. Accordingly, the reactor was further charged with an aqueous solution of triphenylsulfonium chloride [142.8 g (0.49 mole/1.25 equivalents) of triphenylsulfonium chloride and 150 mL of water], followed by stirring at room temperature for 0.5 hour (triphenylsulfonium chloride was used in an amount of 285.7 g (0.96 mole/2.5 equivalents) in total and the reaction time was 1.5 hours in total.). The reaction solution was analyzed by using nuclear magnetic resonance (NMR), by which the raw material was detected being consumed. Thereafter, the reaction solution was separated. The obtained water layer was extracted three times with 100 mL of chloroform while distilling a solvent out of the obtained organic layer, thereby obtaining 328.2 g of the target triphenylsulfonium 2-hydroxy-1,1-difluoroethanesulfonate. In this case, purity was 48% and yield was 97%.

In order to achieve an onium-salt exchange, it is thus required to use a monovalent onium salt represented by $Q^+X^-$ (the formula [7]) in an amount not less than 2 equivalents.

Properties of triphenylsulfonium 2-hydroxy-1,1-difluoroethanesulfonate $^1$H NMR (Solvent for measurement: Deuterated DMSO, Reference material: Tetramethylsilane); δ=7.92-7.65 (m, 15H, Ph$_3$S$^+$), 3.81 (t, J=16.0 Hz, 2H; CH$_2$).

$^{19}$F NMR (Solvent for measurement: Deuterated DMSO, Reference material: Trichlorofluoromethane); δ=−115.47 (t, J=16.0 Hz, 2F; CF$_2$).

Comparative Example 7-1

[Production of triphenylsulfonium 1,1-difluoro-2-(2-methacryloyloxy)-ethanesulfonate] (a 7'th Step: an Esterification Step 2)

[Chemical Formula 74]

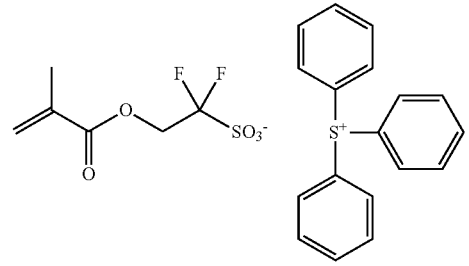

A 2 L reactor was charged with 300.7 g (48% purity, 0.34 mole) of triphenylsulfonium 2-hydroxy-1,1-difluoroethanesulfonate, 700 mL of acetonitrile, 104.8 g (0.68 mole/2 equivalents) of methacrylic anhydride, 8.3 g (0.07 mole/0.2 equivalent) of 4-dimethylaminopyridine, 34.4 g (0.34 mole/1 equivalent) of triethylamine and 60 mg (0.18 millimoles) of nonflex MBP, followed by stirring at 50° C. for 2 hours. Then, a solvent was distilled off and 500 mL of chloroform was added thereto, thereby obtaining a chloroform solution. Thereafter, the chloroform solution was distilled off, followed by rinsing with diluted hydrochloric acid and water. The obtained organic substance was rinsed three times with 300 mL of diisopropyl ether, followed by adding 60 mg (0.18 millimoles) of nonflex MBP and 300 mL of methyl ethyl ketone. The remaining diisopropyl ether was distilled off, thereby obtaining 129.5 g of the target triphenylsulfonium 1,1-difluoro-2-(2-methacryloyloxy)-ethanesulfonate serving as a viscous liquid. This liquid had difficulty in crystallizing, so that a further purification could not be achieved. Accordingly, the liquid was diluted with methyl ethyl ketone thereby obtaining 440.5 g of 29.4 wt % methyl ethyl ketone solution. In this case, purity was 98% and yield was 77%.

Thus, the target substance cannot be crystallized by this process, so that it is difficult to further improve the purity.

Test Example 1

Photoacid Generation Function of triphenylsulfonium 2-(1'-adamantane)carbonyloxy-1,1-difluoroethanesulfonate An acetonitrile solution of sodium 2-(1'-adamantane)carbonyloxy-1,1-difluoroethanesulfonate synthesized in Example 8 was prepared to have a concentration of 0.05 mol/L. It was put into a quartz optical cell having an optical path length of 1 cm, followed by irradiation with a light (290 nm) separated from a xenon lamp to conduct actinometry of acid generation. The amount of acid generated was observed by absorption of tetrabromophenol blue at 610 nm. Quantity of light was measured with potassium iron trioxalate to determine quantum yield. With this, it was 0.21 showing a high acid generation function.

Test Example 2

Solubility of triphenylsulfonium 2-(1'-adamantane)carbonyloxy-1,1-difluoroethanesulfonate 1.0 g of sodium 2-(1'-adamantane)carbonyloxy-1,1-difluoroethanesulfonate synthesized in Example 8 was weighed and added to 100 g of propylene glycol methyl ether acetate, followed by stirring. With this, it was completely dissolved.

Application Example 1

A resist was prepared by dissolving 2 parts by weight of triphenylsulfonium 1,1-difluoro-2-(valeryloxy)ethanesulfonate mentioned in Example 7, 100 parts by weight of a polymer having a weight average molecular weight of 15,000, in which hydroxy groups of polyhydroxystyrene have been protected with 15 mol % of 1-ethoxyethyl group and 15 mol % of tert-butoxycarbonyl group, and 0.2 part by weight of isopropanolamine in 600 parts by weight of propylene glycol monomethyl ether acetate.

Application Example 2

A resist was prepared by dissolving 2 parts by weight of triphenylsulfonium 2-(1'-adamantane)carbonyloxy-1,1-difluoroethanesulfonate mentioned in Example 8, 100 parts by weight of a polymer having a weight average molecular weight of 15,000, in which hydroxy groups of polyhydroxystyrene have been protected with 35 mol % of 1-ethoxyethyl group, and 0.2 parts by weight of isopropanolamine in 600 parts by weight of propylene glycol monomethyl ether acetate.

Application Example 3

A resist was prepared by dissolving 5 parts by weight of triphenylsulfonium 2-(1'-adamantane)carbonyloxy-1,1-difluoroethanesulfonate mentioned in Example 8, 100 parts by weight of a terpolymer (weight average molecular weight 12800) of 45 mol % methyladamantanemethacrylate/25 mol % hydroxyadamantanemethacrylate/30 mol γ-butyrolactonemethacrylate, and 0.1 parts by weight of triethanolamine in 800 parts by weight of propylene glycol monomethyl ether acetate.

Test Example 3

The resists of Application Examples 1, 2 and 3 were filtered by a membrane filter of 0.2 μm to prepare radiosensitive resin composition solutions. Then, the composition solutions were applied on silicon wafers with a rotation speed of 1500 rpm. Then, they were dried at 100° C. for 90 seconds on a hot plate to form resist films having a film thickness of 320 nm. The obtained films were homogeneous and good.

This resist film was subjected to exposure by using an ultraviolet ray by a high-pressure mercury light. After exposure, heating was conducted on the hot plate at 110° C. for 90 seconds. An immersion phenomenon was conducted for 60 seconds in 2.38% tetramethylammonium hydroxide aqueous solution, and rinse was conducted for 30 seconds with pure water.

As a result, in all of Application Examples 1, 2 and 3 there were obtained rectangular, positive-type, good patterns having less edge roughness.

Regarding sulfonium salts (PAG 1 and 2) represented by the following formulas, there were conducted evaluations of compatibility and resolution when resists were formed.

[Chemical Formula 75]

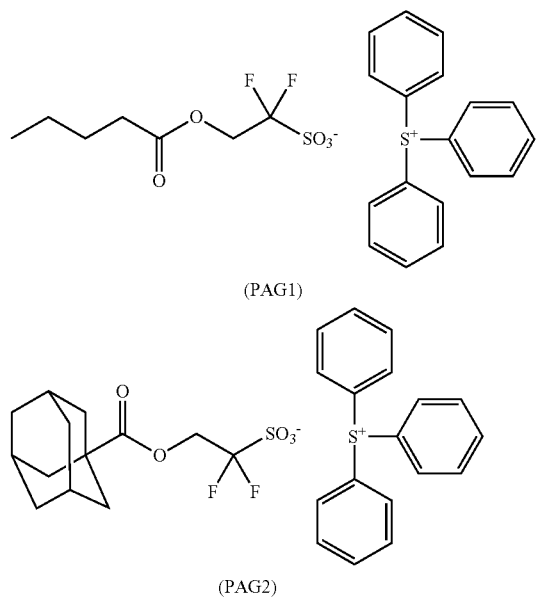

(PAG1)

(PAG2)

Test Examples 4 to 11

Evaluations of PAG Compatibility and Resist Resolution

A resist material was prepared by using a sulfonium salt (PAG 1 or 2) represented by the above formula as an acid generator and a polymer (resin 1-4) represented by the following formula as a base resin. Furthermore, each composition was filtered by a membrane filter of 0.2 μm to prepare each resist solution.

Then, all of the resist solutions were applied on silicon wafers by spin coating to obtain resist films having a film thickness of 250 nm. After conducting a prebaking at 110° C., exposure was conducted with 248 nm ultraviolet ray through a photomask, and then a post-exposure baking was conducted at 120° C. After that, development was conducted at 23° C. for 1 minute by using 2.38 wt % tetramethylammonium hydroxide aqueous solution. Composition and evaluation results of each resist are shown in Table 1.

TABLE 1

| Test Example | Resin (parts by wt.) | Acid Generator (parts by wt.) | Solvent (parts by wt.) | Compatibility | Pattern Shape |
|---|---|---|---|---|---|
| 4 | Resin 1 (40) | PAG1 (1.0) | PGMEA (400) | Good | Clean rectangular |
| 5 | Resin 1 (40) | PAG2 (1.0) | PGMEA (400) | Good | Clean rectangular |
| 6 | Resin 2 (40) | PAG1 (1.0) | PGMEA (400) | Good | Clean rectangular |
| 7 | Resin 2 (40) | PAG2 (1.0) | PGMEA (400) | Good | Clean rectangular |
| 8 | Resin 3 (40) | PAG1 (1.0) | PGMEA (400) | Good | Clean rectangular |
| 9 | Resin 3 (40) | PAG2 (1.0) | PGMEA (400) | Good | Clean rectangular |
| 10 | Resin 4 (40) | PAG1 (1.0) | PGMEA (400) | Good | Clean rectangular |
| 11 | Resin 4 (40) | PAG2 (1.0) | PGMEA (400) | Good | Clean rectangular |

Comparative Examples 8 to 15

For comparison, with respect to sulfonium salts (PAG 3 and 4) represented by the following formulas, evaluations of compatibility of PAG when made into resists and resolution of resists are shown in Table 2.

[Chemical Formula 76]

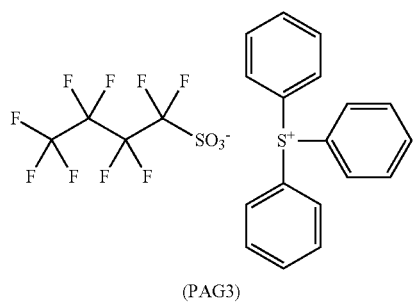

(PAG3)

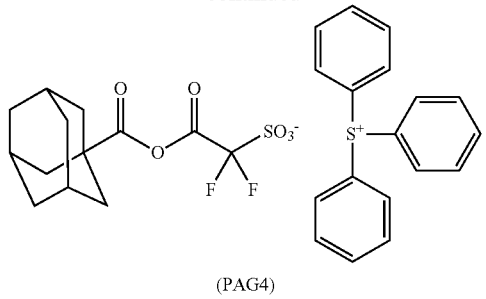

(PAG4)

TABLE 2

| Comparative Example | Resin (parts by wt.) | Acid Generator (parts by wt.) | Solvent (parts by wt.) | Compatibility | Pattern Shape |
|---|---|---|---|---|---|
| 8 | Resin 1 (40) | PAG 3 (1.0) | PGMEA (400) | Good | Somewhat head-swollen shape |
| 9 | Resin 1 (40) | PAG 4 (1.0) | PGMEA (400) | Good | Somewhat distorted rectangular |
| 10 | Resin 2 (40) | PAG 3 (1.0) | PGMEA (400) | Somewhat defective | Somewhat head-swollen shape |
| 11 | Resin 2 (40) | PAG 4 (1.0) | PGMEA (400) | Good | Clean rectangular (inferior to Test Example 7) |
| 12 | Resin 3 (40) | PAG 3 (1.0) | PGMEA (400) | Somewhat defective | Somewhat head-swollen shape |
| 13 | Resin 3 (40) | PAG 4 (1.0) | PGMEA (400) | Good | Clean rectangular (inferior to Test Example 9) |
| 14 | Resin 4 (40) | PAG 3 (1.0) | PGMEA (400) | Somewhat defective | Somewhat head-swollen shape |
| 15 | Resin 4 (40) | PAG 4 (1.0) | PGMEA (400) | Good | Somewhat distorted rectangular (inferior to Test Example 11) |

From the results of Table 1 and Table 2, it was confirmed that the acid generators of the present invention had resolutions higher than those of conventional products.

The invention claimed is:
1. Triphenylsulfonium 1,1-difluoro-2-(2-methacryloyloxy)-ethanesulfonate.

* * * * *